US009246527B2

(12) United States Patent
Okada et al.

(10) Patent No.: US 9,246,527 B2
(45) Date of Patent: Jan. 26, 2016

(54) MEDICAL DIAGNOSTIC SIGNAL DETECTION APPARATUS AND MEDICAL DIAGNOSTIC SIGNAL DETECTION METHOD

(71) Applicant: Hitachi, Ltd., Chiyoda-ku, Tokyo (JP)

(72) Inventors: Yuki Okada, Tokyo (JP); Takashi Oshima, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/595,201

(22) Filed: Jan. 12, 2015

(65) Prior Publication Data

US 2015/0236737 A1  Aug. 20, 2015

(30) Foreign Application Priority Data

Feb. 20, 2014 (JP) ................................. 2014-030163

(51) Int. Cl.
*H04B 1/12* (2006.01)
(52) U.S. Cl.
CPC ....................................... *H04B 1/12* (2013.01)
(58) Field of Classification Search
USPC ................................................. 375/233, 346
See application file for complete search history.

(56) References Cited

U.S. PATENT DOCUMENTS

| 2006/0056352 | A1* | 3/2006 | Proctor et al. ................ 370/332 |
| 2011/0061461 | A1* | 3/2011 | Yoshida ..................... 73/504.12 |
| 2011/0280410 | A1* | 11/2011 | Matono et al. ............... 381/71.1 |
| 2012/0106619 | A1* | 5/2012 | Kawauchi et al. ............ 375/233 |
| 2013/0136233 | A1* | 5/2013 | Okada ............................. 378/62 |
| 2014/0132446 | A1* | 5/2014 | Lennen .................... 342/357.51 |

FOREIGN PATENT DOCUMENTS

JP     04-114637 A      4/1992

OTHER PUBLICATIONS

Oshima, T., et al., "Novel sampling timing background calibration for time-interleaved A/D converters", IEEE $52^{nd}$ International Midwest Symposium on Circuits and Systems, Aug. 2009, pp. 361-364.

* cited by examiner

Primary Examiner — Eva Puente
(74) Attorney, Agent, or Firm — Miles & Stockbridge P.C.

(57) ABSTRACT

In a system including analog circuits of multichannel, channels which have a short distance therebetween are grouped so as to be included in the same group. During a reception period, a common correction signal is supplied to master channels allocated to the respective groups, and received signals are supplied to slave channels other than the master channels. A correction coefficient which tracks a characteristic fluctuation of each group is continuously searched for through continuous comparison between outputs of the respective master channels, and an output of each slave channel is corrected by using the correction coefficient of a group including the slave channel.

15 Claims, 12 Drawing Sheets

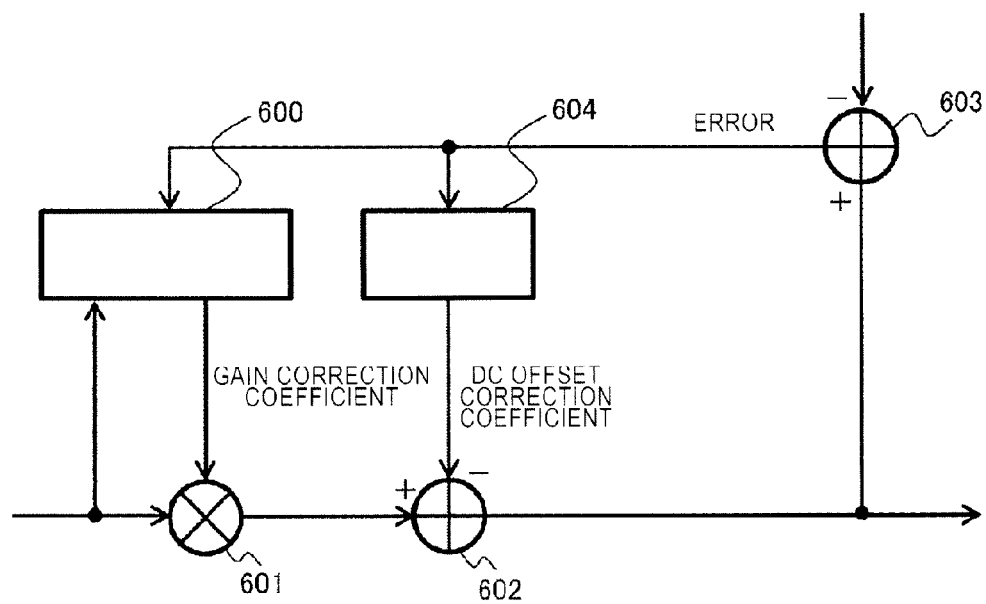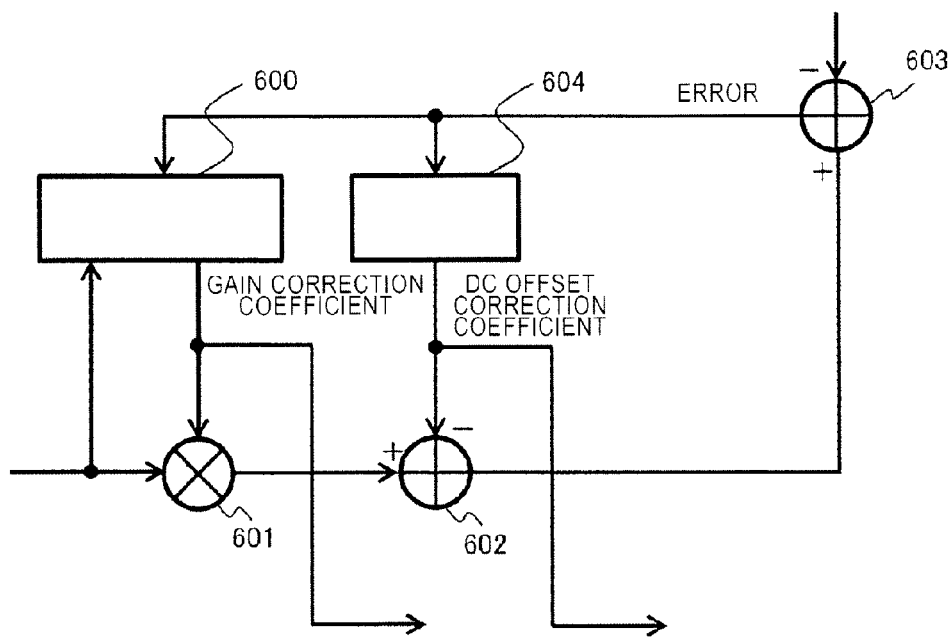

MEDICAL DIAGNOSTIC SIGNAL DETECTION APPARATUS AND MEDICAL DIAGNOSTIC SIGNAL DETECTION METHOD

CROSS-REFERENCE TO RELATED APPLICATION

This is application claims the priority of Japanese Patent Application No. 2014-030163 Filed Feb. 20, 2014, which is incorporated herein by reference in its entirety.

BACKGROUND OF THE INVENTION

1. Field of the Invention

The present invention relates to a medical diagnostic signal detection apparatus and a medical diagnostic signal detection method, and particularly relates to a signal detection apparatus which receives a multichannel signal and a signal detection method therefor.

2. Background Art

In a medical diagnostic apparatus such as an ultrasonic diagnostic apparatus or a sonar, multichannel signals are required to be received in order to obtain a highly accurate image. The total power loss of all channels increases due to the use of multichannel reception circuits. In addition, in a case where multichannel transmission circuits are also necessary as in the ultrasonic diagnostic apparatus, the power loss is also considerable during operations thereof. Therefore, a heat generation problem due to the power loss may be more serious than before. In other words, a temperature fluctuation occurs in a module or an IC chip due to the heat generation, and a power supply voltage fluctuation also occurs as a result of the temperature fluctuation.

A threshold voltage or mobility of a MOS transistor forming a circuit of each channel fluctuates due to the temperature fluctuation. A sa result of the fluctuation and the power supply voltage fluctuation, a gain, a DC offset voltage, and a frequency bandwidth of an amplifier or an analog-digital converter fluctuate. In addition, a delay time of a clock buffer which supplies a sampling clock to the analog-digital converter also fluctuates, and thus sampling timing of the analog-digital converter also fluctuates.

Since a temperature or a power supply voltage cannot be expected to be uniform in all of the channels, a mismatch in the temperature or the power supply voltage between the channels causes mismatches in gain, DC offset voltage, frequency bandwidth, and sampling timing between the channels. As a result, an artifact (false image) is generated in a final image, and thus the accuracy of a medical diagnostic apparatus or a sonar is reduced.

In JP-A-4-114637, in a system including a plurality of channels, a common reference voltage is supplied to the channels during testing of a correction value, and an output value of each channel is acquired. Next, a correction value for correcting a gain mismatch between amplifiers of the respective channels is obtained on the basis of the result.

During reception, a gain of the amplifier of each channel is adjusted by using the correction value obtained during the correction value test as described above, and thus the gain mismatch between the amplifiers is removed. However, in this method, while each channel performs reception, a reference voltage for correction cannot be supplied to the channels, and thus a correction value cannot be tested.

SUMMARY OF THE INVENTION

In the related art, during a period in which a signal is received, a common correction signal cannot be supplied to an input terminal of each channel, and thus a value for correcting a characteristic mismatch between the channels cannot be tested. Therefore, a correction value which is obtained before the reception period has to be used. For this reason, due to a temperature fluctuation or a power supply voltage fluctuation during the reception period, inconsistency, that is, a deviation occurs between a correction value which is used and an actual characteristic mismatch amount. As a result, a characteristic mismatch remains between outputs of the respective channels, and thus an artifact is generated in an image.

In a system including analog circuits of multichannels, for example, channels are grouped into a plurality of groups so that the channels which have a short distance therebetween are included in the same group. A single channel of each group is designated as a "master" channel which does not perform reception and is used only to search for a correction coefficient.

During a signal reception period, a common correction signal is supplied to the master channels of the respective groups, and received signals are supplied to respective "slave" channels other than the master channels. An "intergroup correction coefficient" which tracks a characteristic fluctuation of each group is continuously searched for through continuous comparison between outputs of the master channels of the respective groups during the reception period. In addition, during the reception period, an output of each slave channel is corrected by using the inter-group correction coefficient of a group including the slave channel.

During reception of a signal in each channel, a signal output can be corrected in tracking of a temperature fluctuation or a power supply voltage fluctuation. Therefore, a characteristic mismatch between channels can be stably removed, and thus it is possible to minimize the occurrence of an artifact in an image.

BRIEF DESCRIPTION OF THE DRAWINGS

FIG. 3 is a diagram illustrating Example 3 of the present invention.

FIG. 4 is a diagram illustrating Example 4 of the present invention.

DETAILED DESCRIPTION OF THE INVENTION

Example 1

Figure 1:
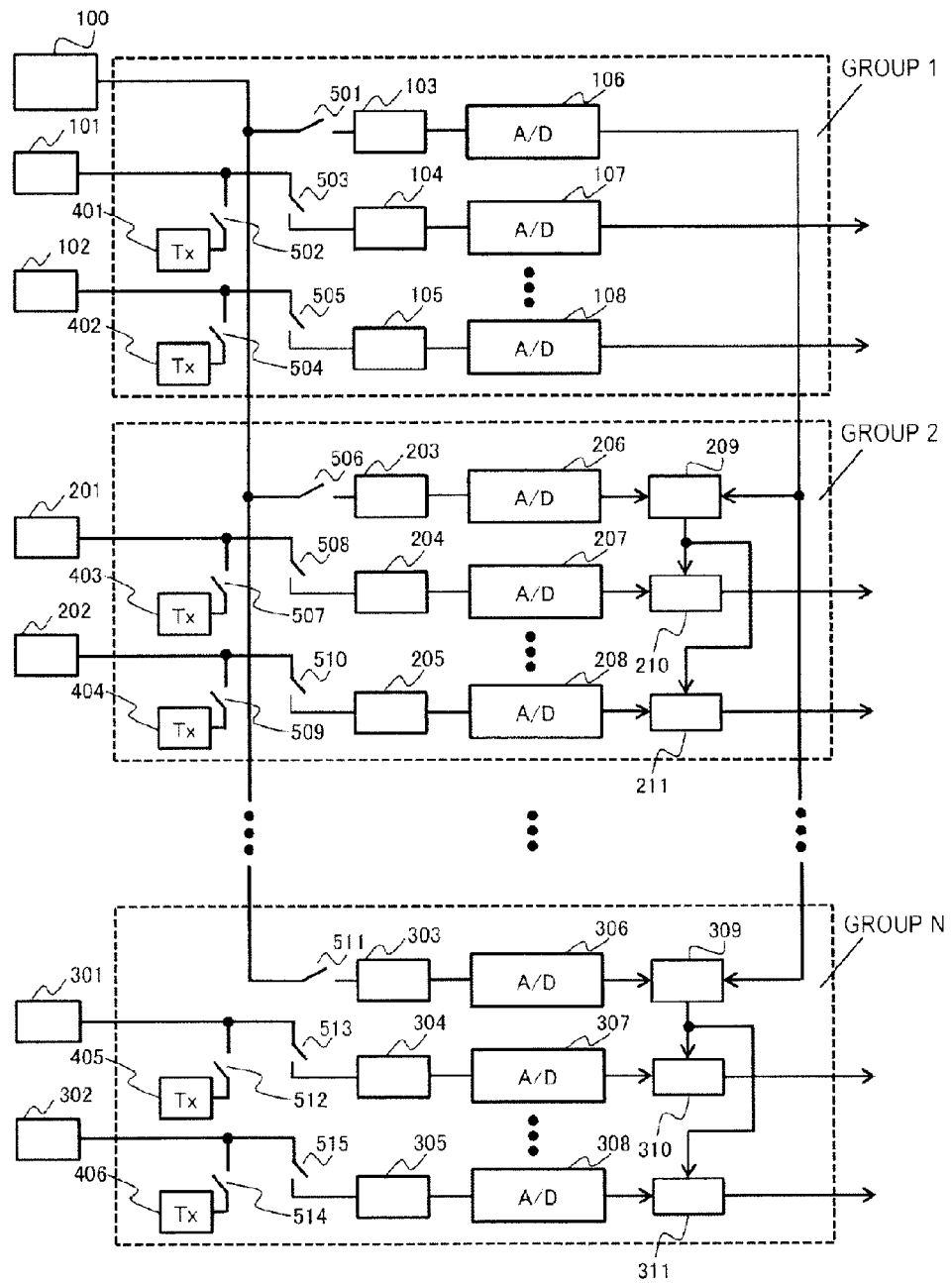
FIG. 1 is a diagram illustrating Example 1 of the present invention.

Example 1 of the present invention will be described with reference to FIG. 1.

A first concept of the present invention is as follows. First, in a system including multichannel analog circuits, for example, channels are grouped into N groups so that channels which are physically close to each other are included in the same group.

A channel shown on the top side of each group is designated as a "master" channel which does not perform reception and is used only to search for a correction coefficient. During a signal reception period, a common inter-group correction signal is supplied to the master channels of the respective groups, and received signals are supplied to respective "slave" channels other than the master channels.

During the reception period, outputs of the master channels of the respective groups are continuously compared with each other, and thus an "inter-group correction coefficient" which tracks a characteristic fluctuation of each group is continuously searched for. In addition, during the signal reception period, an output of each slave channel is corrected by using the inter-group correction coefficient of a group including the slave channel. In the present example, a method is disclosed in which the first concept of the present invention is realized by an ultrasonic diagnostic apparatus. Hereinafter, details of a configuration and an operation thereof will be described.

A reception portion of each channel includes an amplifier and an analog-digital converter (A/D) subsequent thereto. Each group includes M (where M is a natural number) channels, in which, for example, the uppermost channel is a master channel, and the other channels are slave channels. This is illustrated in FIG. 1. The number M of channels included in each group is not required to be the same and may be different, and, for convenience of description, M channels are used in all groups. It is noted that channels relatively close to each other at mutual physical distances are grouped so as to be included in the same group, and thus temperature fluctuations and power supply voltage fluctuations of all the channels included in the same group are regarded to be substantially at the same level.

First, connections of the master channels will be described. An output of an inter-group correction signal generator 100 is input to an amplifier 103 via a switch 501, and an output of the amplifier 103 is input to an analog-digital converter 106. Here, the amplifier 103 and the analog-digital converter 106 form a master channel of a group 1, and the master channel is especially referred to as a "top master" channel.

Similarly, the output of the inter-group correction signal generator 100 is input to an amplifier 203 via a switch 506, and an output of the amplifier 203 is input to an analog-digital converter 206. Here, the amplifier 203 and the analog-digital converter 206 form a master channel of a group 2.

Similarly, the output of the inter-group correction signal generator 100 is input to an amplifier 303 via a switch 511, and an output of the amplifier 303 is input to an analog-digital converter 306. Here, the amplifier 303 and the analog-digital converter 306 form a master channel of a group 3.

Next, connections of the slave channels will be described. A transmission circuit 401 is connected to a piezoelectric element 101 via a switch 502. In addition, the piezoelectric element 101 is also connected to an amplifier 104 via a switch 503. An output of the amplifier 104 is input to an analog-digital converter 107. Here, the transmission circuit 401 is a transmission circuit of a slave channel 1 of the group 1. Further, the amplifier 104 and the analog-digital converter 107 form a reception circuit of the slave channel 1 of the group 1. An output of the analog-digital converter 107 is used as an output of the slave channel 1 of the group 1 as it is without undergoing inter-group correction.

Similarly, a transmission circuit 402 is connected to a piezoelectric element 102 via a switch 504. In addition, the piezoelectric element 102 is also connected to an amplifier 105 via a switch 505. An output of the amplifier 105 is input to an analog-digital converter 108. Here, the transmission circuit 402 is a transmission circuit of a slave channel M-1 of the group 1. Further, the amplifier 105 and the analog-digital converter 108 form a reception circuit of the slave channel M-1 of the group 1. An output of the analog-digital converter 108 is used as an output of the slave channel M-1 of the group 1 as it is without undergoing inter-group correction.

Similarly, a transmission circuit 403 is connected to a piezoelectric element 201 via a switch 507. In addition, the piezoelectric element 201 is also connected to an amplifier 204 via a switch 508. An output of the amplifier 204 is input to an analog-digital converter 207. Here, the transmission circuit 403 is a transmission circuit of a slave channel 1 of the group 2. Further, the amplifier 204 and the analog-digital converter 207 form a reception circuit of the slave channel 1 of the group 2.

Similarly, a transmission circuit 404 is connected to a piezoelectric element 202 via a switch 509. In addition, the piezoelectric element 202 is also connected to an amplifier 205 via a switch 510. An output of the amplifier 205 is input to an analog-digital converter 208. Here, the transmission circuit 404 is a transmission circuit of a slave channel M-1 of the group 2. Further, the amplifier 205 and the analog-digital converter 208 form a reception circuit of the slave channel M-1 of the group 2.

Similarly, a transmission circuit 405 is connected to a piezoelectric element 301 via a switch 512. In addition, the piezoelectric element 301 is also connected to an amplifier 304 via a switch 513. An output of the amplifier 304 is input to an analog-digital converter 307. Here, the transmission circuit 405 is a transmission circuit of a slave channel 1 of the group N. Further, the amplifier 304 and the analog-digital converter 307 form a reception circuit of the slave channel 1 of the group N.

Similarly, a transmission circuit 406 is connected to a piezoelectric element 302 via a switch 514. In addition, the piezoelectric element 302 is also connected to an amplifier 305 via a switch 515. An output of the amplifier 305 is input to an analog-digital converter 308. Here, the transmission circuit 406 is a transmission circuit of a slave channel M-1 of the group N. Further, the amplifier 305 and the analog-digital converter 308 form a reception circuit of the slave channel M-1 of the group N.

Next, connections related to inter-group digital correction will be described. An output (an output of the top master channel) of the analog-digital converter 106 and an output (an output of the master channel of the group 2) of the analog-digital converter 206 are input to an inter-group correction coefficient search portion 209. An output (an uncorrected output of the slave channel 1 of the group 2) of the analog-digital converter 207 is input to an inter-group correction portion 210. An output of the inter-group correction coefficient search portion 209 is also input to the inter-group correction portion 210. An output of the inter-group correction portion 210 is a corrected output of the slave channel 1 of the group 2.

In addition, an output (an uncorrected output of the slave channel M-1 of the group 2) of the analog-digital converter 208 is input to an inter-group correction portion 211. The output of the inter-group correction coefficient search portion 209 is also input to the inter-group correction portion 211. An output of the inter-group correction portion 211 is a corrected output of the slave channel M-1 of the group 2.

Similarly, an output (an output of the top master channel) of the analog-digital converter 106 and an output (an output of the master channel of the group N) of the analog-digital converter 306 are input to an inter-group correction coefficient search portion 309. An output (an uncorrected output of the slave channel 1 of the group N) of the analog-digital converter 307 is input to an inter-group correction port ion 310. An output of the inter-group correction coefficient search portion 309 is also input to the inter-group correction portion 310. An output of the inter-group correction portion 310 is a corrected output of the slave channel 1 of the group N.

In addition, an output (an uncorrected output of the slave channel M-1 of the group N) of the analog-digital converter 308 is input to an inter-group correction portion 311. The output of the inter-group correction coefficient search portion 309 is also input to the inter-group correction portion 311. An output of the inter-group correction portion 311 is a corrected output of the slave channel M-1 of the group N.

In addition, the same connections and configurations are applied to the slave channel 2 to the slave channel M-2 and the group 3 to the group N-1, which are not illustrated.

Next, each operation will be described. First, an inter-group correction coefficient search operation will be described. The switches 501, 506 and 511 are turned on, and thus an inter-group correction signal generated by the inter-group correction signal generator 100 is simultaneously input to the top master channel and each master channel of the group 2 to the group N. The signal is amplified by the amplifier of each channel, and is then converted from an analog signal to a digital signal by the analog-digital converter. In addition, an output of the analog-digital converter of the top master channel and an output of the analog-digital converter of the master channel of the group 2 are input to the inter-group correction coefficient search portion 209, and the inter-group correction coefficient search portion 209 searches for a mismatch amount of a circuit characteristic of the group 2 relative to the group 1 on the basis of a difference between both of the outputs. The obtained search value is supplied from the inter-group correction coefficient search portion 209 to the inter-group correction portions 210 and 211 of the respective slave channels of the group 2 as a correction coefficient.

Similarly, the output of the analog-digital converter of the top master channel and an output of the analog-digital converter of the master channel of the group N are input to the inter-group correction coefficient search portion 309, and the inter-group correction coefficient search portion 309 searches for a mismatch amount of a circuit characteristic of the group N relative to the group 1 on the basis of a difference between both of the outputs. The obtained search value is supplied from the inter-group correction coefficient search portion 309 to the inter-group correction portions 310 and 311 of the respective slave channels of the group N as a correction coefficient. In addition, in the group 3 to the group N-1, the above-described inter-group correction coefficient search is also made. Further, the mismatch amount of the circuit characteristic is a mismatch amount in gain, DC offset voltage, frequency bandwidth, sampling timing, or the like of the other groups relative to the group 1.

Next, transmission and reception operations will be described. During a transmission period, the switches 502, 504, 507, 509, 512 and 514 are turned on, and thus a high voltage pulse or a high voltage analog signal generated by the transmission circuit of the slave channel of each group is applied to each piezoelectric element. The piezoelectric element converts the applied high voltage into vibration due to a piezoelectric effect. The piezoelectric element is pressed to a body surface of a subject (a human body which undergoes ultrasonic diagnosis), and thus the vibration propagates through the body via the body surface as ultrasonic waves. The above description relates to the transmission operation.

The ultrasonic waves which propagate through the body are reflected in a complicated manner by the organs of the body, and are then received by the respective piezoelectric elements of the slave channels via the body surface again. The piezoelectric elements convert the received reflected waves of the ultrasonic waves into electric signals due to the piezoelectric effect. During the reception period, the switches 501, 506, 511, 503, 505, 508, 510, 513 and 515 are turned on, and the switches 502, 504, 507, 509, 512 and 514 are turned off. Each of the received signals which are converted into the electric signals by the piezoelectric elements of the respective slave channels is input to the amplifier so as to undergo signal amplification, and is then converted from an analog signal to a digital signal by the subsequent analog-digital converter.

In the slave channels included in the groups other than the group 1, inter-group digital correction is performed as follows. In other words, in a case of the slave channels of the group 2, the signal digitalized by the analog-digital converter is corrected through a digital calculation process by the subsequent inter-group correction portion. A correction coefficient used for the correction is supplied from the inter-group correction coefficient search portion 209 through the inter-group correction coefficient search operation.

Therefore, in an output of the inter-group correction portion of each slave channel of the group 2, a mismatch in gain, DC offset voltage, frequency bandwidth, sampling timing, or the like of the group 2 relative to the group 1 is corrected by using a corresponding correction coefficient. Similarly, in a case of the slave channels of the group N, the signal digitalized by the analog-digital converter is corrected through a digital calculation process by the subsequent inter-group correction portion. A correction coefficient used for the correction is supplied from the inter-group correction coefficient search portion 309 through the inter-group correction coefficient search operation.

Therefore, in an output of the inter-group correction portion of each slave channel of the group N, a mismatch in gain, DC offset voltage, frequency bandwidth, sampling timing, or the like of the group N relative to the group 1 is corrected by using a corresponding correction coefficient.

The various mismatches are caused by the following. In other words, power consumption increases with the increase in the number of multichannels, and thus a temperature fluctuation occurs due to heat generation. In addition, a power supply voltage also fluctuates due to the temperature fluctuation. Due to the temperature fluctuation, a threshold voltage or mobility of the amplifier of each channel or a MOS transistor forming the analog-digital converter fluctuates. As a result of the fluctuation and the power supply voltage fluctuation, a gain, a DC offset voltage, and a frequency bandwidth of an amplifier or an analog-digital converter fluctuate.

In addition, the delay time of a clock buffer which supplies a sampling clock to the analog-digital converter also fluctuates, and thus the sampling timing of the analog-digital converter also fluctuates. The way in which the temperature fluctuation or the power supply voltage fluctuation occurs may differ depending on each location in a module or a chip which stores multichannels therein. However, as described above, the channels which are close to each other are grouped so as to be included in the same group, and thus it can be expected that the way in which the temperature fluctuation or the power supply voltage fluctuation occurs is regarded to be uniform in all of the channels included in the same group.

The above-described inter-group correction coefficient search operation is continuously performed at all times including the reception period. The top master channel or the master channels of the group 2 and the subsequent groups are not required to receive ultrasonic signals, and may thus be used only for the inter-group correction coefficient search operation even during the reception period. For this reason, during the reception period, the search for an inter-group correction coefficient of each group is continuously made in the background in which each slave channel performs a reception process of the ultrasonic signal. Temperatures and power supply voltages in the same group can be regarded to be uniform, and thus an inter-group correction coefficient of each group is effective for correction of all the slave channels included in the group. In addition, an inter-group correction coefficient of each group is continuously searched for even during the reception period and can thus track a temperature fluctuation or a power supply voltage fluctuation. Therefore, during the reception period, a characteristic mismatch between the channels can be stably removed, and thus it is possible to minimize the occurrence of an artifact in an image.

The above description relates to the Example of the ultrasonic diagnostic apparatus, but the same configuration is employed in the case of a sonar, and thus the same embodiment of the present invention is possible. In addition, medical diagnostic apparatuses such as an X-ray CT apparatus, a PET, and an SPECT are also systems which receive multichannel signals as described above, and the same embodiment of the present invention is possible by omitting the transmission circuit and portions which perform a transmission operation from the present example and by replacing each piezoelectric element with a photodiode for receiving an X-ray signal or a gamma-ray signal.

Example 2

Figure 2:
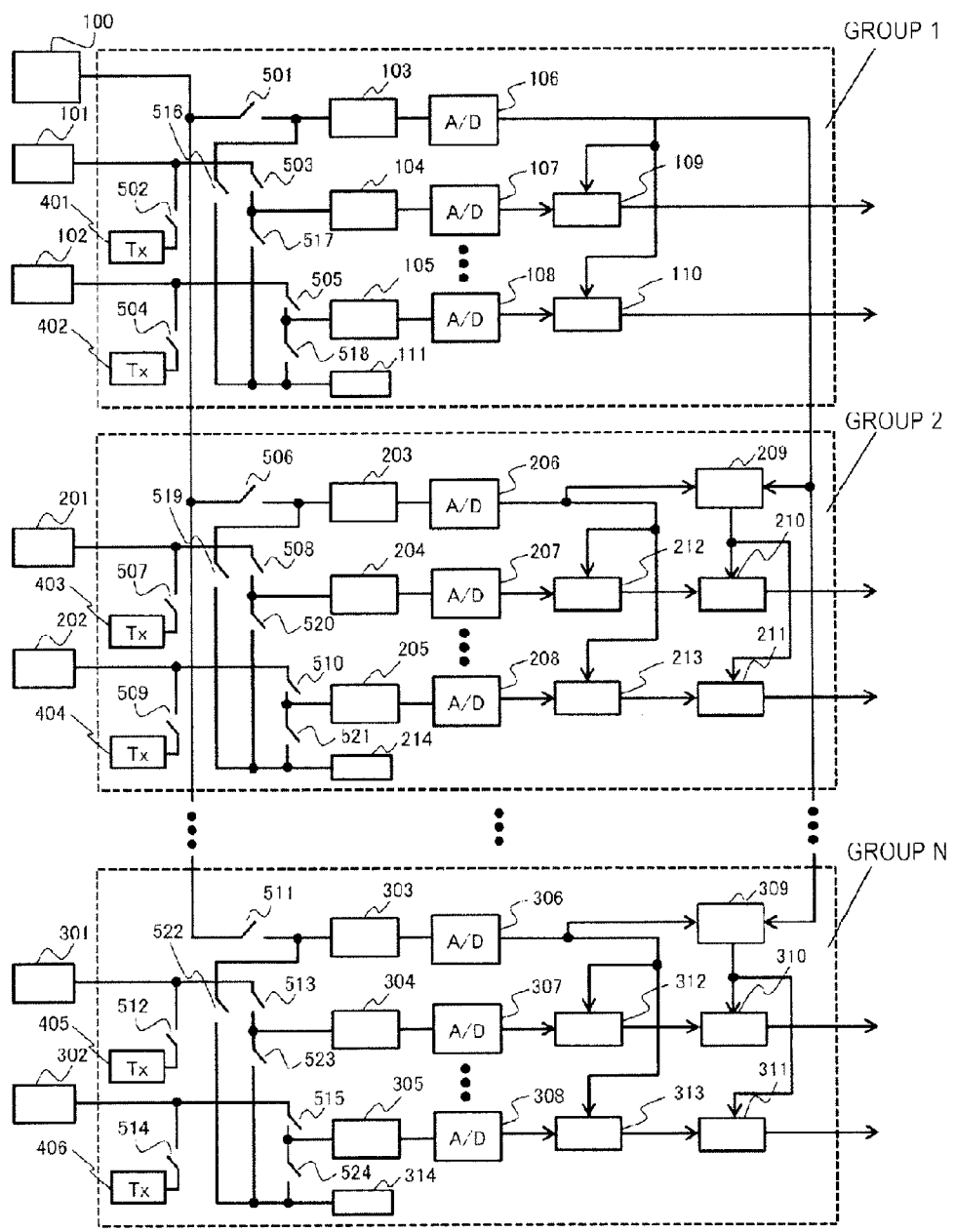
FIG. 2 is a diagram illustrating Example 2 of the present invention.

With reference to FIG. 2, Example 2 of the present invention will be described. In the same manner as in Example 1, the first concept of the present invention is realized as follows. In other words, in a system including multichannel analog circuits, for example, channels are grouped into N groups so that channels which have a short distance therebetween are included in the same group.

A channel shown on the top side of each group is designated as a "master" channel which does not perform reception and is used only to search for a correction coefficient. During a signal reception period, a common inter-group correction signal is supplied to the master channels of the respective groups, and received signals are supplied to respective "slave" channels other than the master channels. During the reception period, outputs of the master channels of the respective groups are continuously compared with each other, and thus an "inter-group correction coefficient" which tracks a characteristic fluctuation of each group is continuously searched for. In addition, during the signal reception period, an output of each slave channel is corrected by using the inter-group correction coefficient of a group including the slave channel.

In the present example, as a second concept of the present invention, in periods other than a reception period, an "intra-group correction coefficient" for correcting a characteristic mismatch between a master channel and each slave channel in a group including the master channel is searched for.

The coefficient is searched for by supplying a common intra-group correction signal to the master channel and the slave channels in the group, and comparing outputs thereof. During the reception period, correction is performed on an output of each slave channel by using the intra-group correction coefficient along with correction using the above-described inter-group correction coefficient. In the present example, a method is disclosed in which the first and second concepts of the present invention are realized by exemplifying an ultrasonic diagnostic apparatus. Hereinafter, details of a configuration and an operation thereof will be described.

A reception portion of each channel includes an amplifier and an analog-digital converter (A/D) subsequent thereto. Each group includes M channels, in which the uppermost channel is a master channel, and the other channels are slave channels. The number of channels included in each group is not required to be the same and may be different, and, for convenience of description, M channels are used in all groups. It is noted that channels which have a short distance therebetween are included in the same group, and thus temperature fluctuations and power supply voltage fluctuations of all the channels included in the same group are regarded to be substantially at the same level.

First, connections of the master channels will be described. An output of an inter-group correction signal generator 100 is input to an amplifier 103 via a switch 501, and an output of the amplifier 103 is input to an analog-digital converter 106. Here, the amplifier 103 and the analog-digital converter 106 form a master channel of a group 1, and the master channel is especially a top master channel.

Similarly, the output of the inter-group correction signal generator 100 is input to an amplifier 203 via a switch 506, and an output of the amplifier 203 is input to an analog-digital converter 206. Here, the amplifier 203 and the analog-digital converter 206 form a master channel of a group 2.

Similarly, the output of the inter-group correction signal generator 100 is input to an amplifier 303 via a switch 511, and an output of the amplifier 303 is input to an analog-digital converter 306. Here, the amplifier 303 and the analog-digital converter 306 form a master channel of a group 3.

Next, connections of the slave channel will be described. A transmission circuit 401 is connected to a piezoelectric element 101 via a switch 502. In addition, the piezoelectric element 101 is also connected to an amplifier 104 via a switch 503. An output of the amplifier 104 is input to an analog-digital converter 107. Here, the transmission circuit 401 is a transmission circuit of a slave channel 1 of the group 1. Further, the amplifier 104 and the analog-digital converter 107 form a reception circuit of the slave channel 1 of the group 1.

Similarly, a transmission circuit 402 is connected to a piezoelectric element 102 via a switch 504. In addition, the piezoelectric element 102 is also connected to an amplifier 105 via a switch 505. An output of the amplifier 105 is input to an analog-digital converter 108. Here, the transmission circuit 402 is a transmission circuit of a slave channel M-1 of the group 1. Further, the amplifier 105 and the analog-digital converter 108 form a reception circuit of the slave channel M-1 of the group 1.

Similarly, a transmission circuit 403 is connected to a piezoelectric element 201 via a switch 507. In addition, the piezoelectric element 201 is also connected to an amplifier 204 via a switch 508. An output of the amplifier 204 is input to an analog-digital converter 207. Here, the transmission circuit 403 is a transmission circuit of a slave channel 1 of the group 2. Further, the amplifier 204 and the analog-digital converter 207 form a reception circuit of the slave channel 1 of the group 2.

Similarly, a transmission circuit 404 is connected to a piezoelectric element 202 via a switch 509. In addition, the piezoelectric element 202 is also connected to an amplifier 205 via a switch 510. An output of the amplifier 205 is input to an analog-digital converter 208. Here, the transmission circuit 404 is a transmission circuit of a slave channel M-1 of the group 2. Further, the amplifier 205 and the analog-digital converter 208 form a reception circuit of the slave channel M-1 of the group 2.

Similarly, a transmission circuit 405 is connected to a piezoelectric element 301 via a switch 512. In addition, the piezoelectric element 301 is also connected to an amplifier 304 via a switch 513. An output of the amplifier 304 is input to an analog-digital converter 307. Here, the transmission circuit 405 is a transmission circuit of a slave channel 1 of the group N. Further, the amplifier 304 and the analog-digital converter 307 form a reception circuit of the slave channel 1 of the group N.

Similarly, a transmission circuit 406 is connected to a piezoelectric element 302 via a switch 514. In addition, the piezoelectric element 302 is also connected to an amplifier 305 via a switch 515. An output of the amplifier 305 is input to an analog-digital converter 308. Here, the transmission circuit 406 is a transmission circuit of a slave channel M-1 of the group N. Further, the amplifier 305 and the analog-digital converter 308 form a reception circuit of the slave channel M-1 of the group N.

In the present example, an intra-group correction signal generator 111 for use in the group 1 is further provided, and an output terminal thereof is connected to input terminals of the amplifiers 103, 104 and 105 of the master (top master) channel and the respective slave channels of the group 1 via the switches 516, 517 and 518.

Similarly, an intra-group correction signal generator 214 for use in the group 2 is further provided, and an output terminal thereof is connected to input terminals of the amplifiers 203, 204 and 205 of the master channel and the respective slave channels of the group 2 via the switches 519, 520 and 521.

Similarly, an intra-group correction signal generator 314 for use in the group N is further provided, and an output terminal thereof is connected to input terminals of the amplifiers 303, 304 and 305 of the master channel and the respective slave channels of the group N via the switches 522, 523 and 524.

Next, configurations related to inter-group digital correction and intra-group digital correction will be described. In the present example, an intra-group correction portion is provided in addition to the inter-group correction portion of Example 1. An output (an output of the top master channel) of the analog-digital converter 106 and an output (an output of the master channel of the group 2) of the analog-digital converter 206 are input to an inter-group correction coefficient search portion 209. The inter-group correction coefficient search portion 209 outputs an inter-group correction coefficient of the group 2 to the inter-group correction portions 210 and 211. Similarly, an output (an output of the top master channel) of the analog-digital converter 106 and an output (an output of the master channel of the group N) of the analog-digital converter 306 are input to an inter-group correction coefficient search portion 309. The inter-group correction coefficient search portion 309 outputs an inter-group correction coefficient of the group N to the inter-group correction portions 310 and 311.

An output of the analog-digital converter 107 of the slave channel 1 of the group 1 is input to an intra-group correction portion 109. The output of the master (top master) channel of the group 1 is also input to the intra-group correction portion 109. An output of the intra-group correction portion 109 is a corrected output of the slave channel 1 of the group 1. In addition, an output of the analog-digital converter 108 of the slave channel M-1 of the group 1 is input to an intra-group correction portion 110. The output of the master (top master) channel of the group 1 is also input to the intra-group correction portion 110. An output of the intra-group correction portion 110 is a corrected output of the slave channel M-1 of the group 1.

An output of the analog-digital converter 207 of the slave channel 1 of the group 2 is input to an intra-group correction portion 212. An output of the master channel of the group 2 is also input to the intra-group correction portion 212. An output of the intra-group correction portion 212 is input to an inter-group correction portion 210. An output of the inter-group correction portion 210 is a corrected output of the slave channel 1 of the group 2. Similarly, an output of the analog-digital converter 208 of the slave channel M-1 of the group 2 is input to an intra-group correction portion 213. The output of the master channel of the group 2 is also input to the intra-group correction portion 213. An output of the intra-group correction portion 213 is input to an inter-group correction portion 211. An output of the inter-group correction portion 211 is a corrected output of the slave channel M-1 of the group 2.

An output of the analog-digital converter 307 of the slave channel 1 of the group N is input to an intra-group correction portion 312. An output of the master channel of the group N is also input to the intra-group correction portion 312. An output of the intra-group correction portion 312 is input to an inter-group correction portion 310. An output of the inter-group correction portion 310 is a corrected output of the slave channel 1 of the group N. Similarly, an output of the analog-digital converter 308 of the slave channel M-1 of the group N is input to an intra-group correction portion 313. The output of the master channel of the group N is also input to the intra-group correction portion 313. An output of the intra-group correction portion 313 is input to an inter-group correction portion 311. An output of the inter-group correction portion 311 is a corrected output of the slave channel M-1 of the group N.

In addition, the same connections and configurations are applied to the slave channel 2 to the slave channel M-2 and the group 3 to the group N-1, which are not illustrated.

Next, each operation will be described. First, an intra-group correction coefficient search operation which is a feature of the present example will be described. The intra-group correction coefficient search operation is performed in periods other than the reception period. Not only the master channel but also each slave channel participates in the intra-group correction coefficient search, and thus reception cannot be performed during that time. During the intra-group correction coefficient search, the switches 516, 517, 518, 519, 520, 521, 522, 523 and 524 are turned on, and the switches 501, 506, 511, 503, 505, 508, 510, 513 and 515 are turned off.

Consequently, an intra-group correction signal generated by the intra-group correction signal generator 111 for use in the group 1 is input to the amplifiers of the master (top master)

channel and each slave channel of the group 1. The signal is amplified by the amplifier of each channel, and is then converted from an analog signal to a digital signal by the analog-digital converter. In addition, an output of the analog-digital converter of the slave channel 1 of the group 1 and an output of the master (top master) channel of the group 1 are input to the intra-group correction portion 109, and the intra-group correction portion 109 searches for a mismatch amount of a circuit characteristic of the slave channel 1 of the group 1 relative to the master (top master) channel of the group 1 on the basis of a difference between both of the outputs, and an obtained search value is stored in the intra-group correction portion 109 as a correction coefficient.

Similarly, an output of the analog-digital converter of the slave channel M-1 of the group 1 and an output of the master (top master) channel of the group 1 are input to the intra-group correction portion 110, and the intra-group correction portion 110 searches for a mismatch amount of a circuit characteristic of the slave channel M-1 of the group 1 relative to the master (top master) channel of the group 1 on the basis of a difference between both of the outputs, and an obtained search value is stored in the intra-group correction portion 110 as a correction coefficient.

Similarly, an intra-group correction signal generated by the intra-group correction signal generator 214 for use in the group 2 is input to the amplifiers of the master channel and each slave channel of the group 2. The signal is amplified by the amplifier of each channel, and is then converted from an analog signal to a digital signal by the analog-digital converter.

In addition, an output of the analog-digital converter of the slave channel 1 of the group 2 and an output of the master channel of the group 2 are input to the intra-group correction portion 212, and the intra-group correction portion 212 searches for a mismatch amount of a circuit characteristic of the slave channel 1 of the group 2 relative to the master channel of the group 2 on the basis of a difference between both of the outputs, and an obtained search value is stored in the intra-group correction portion 212 as a correction coefficient. Similarly, an output of the analog-digital converter of the slave channel M-1 of the group 2 and an output of the master channel of the group 2 are input to the intra-group correction portion 213, and the intra-group correction portion 213 searches for a mismatch amount of a circuit characteristic of the slave channel M-1 of the group 2 relative to the master channel of the group 2 on the basis of a difference between both of the outputs, and an obtained search value is stored in the intra-group correction portion 213 as a correction coefficient.

Similarly, an intra-group correction signal generated by the intra-group correction signal generator 314 for use in the group N is input to the amplifiers of the master channel and each slave channel of the group N. The signal is amplified by the amplifier of each channel, and is then converted from an analog signal to a digital signal by the analog-digital converter.

In addition, an output of the analog-digital converter of the slave channel 1 of the group N and an output of the master channel of the group N are input to the intra-group correction portion 312, and the intra-group correction portion 312 searches for a mismatch amount of a circuit characteristic of the slave channel 1 of the group N relative to the master channel of the group N on the basis of a difference between both of the outputs, and an obtained search value is stored in the intra-group correction portion 312 as a correction coefficient.

Similarly, an output of the analog-digital converter of the slave channel M-1 of the group N and an output of the master channel of the group N are input to the intra-group correction portion 313, and the intra-group correction portion 313 searches for a mismatch amount of a circuit characteristic of the slave channel M-1 of the group N relative to the master channel of the group N on the basis of a difference between both of the outputs, and an obtained search value is stored in the intra-group correction portion 313 as a correction coefficient. In addition, the slave channel 2 to the slave channel M-2 and the group 3 to the group N-1, which are not illustrated, also search for the intra-group correction coefficients as mentioned above.

Further, the mismatch amount of the circuit characteristic is a mismatch amount in gain, DC offset voltage, frequency bandwidth, sampling timing, or the like of the slave channel relative to the master channel.

Next, an inter-group correction coefficient search operation will be described. The switches 501, 506 and 511 are turned on, and thus an inter-group correction signal generated by the inter-group correction signal generator 100 is simultaneously input to the top master channel and each master channel of the group 2 to the group N. The signal is amplified by the amplifier of each channel, and is then converted from an analog signal to a digital signal by the analog-digital converter.

In addition, an output of the analog-digital converter of the top master channel and an output of the analog-digital converter of the master channel of the group 2 are input to the inter-group correction coefficient search portion 209, and the inter-group correction coefficient search portion 209 searches for a mismatch amount of a circuit characteristic of the group 2 relative to the group 1 on the basis of a difference between both of the outputs. The obtained search value is supplied from the inter-group correction coefficient search portion 209 to the inter-group correction portions 210 and 211 of the respective slave channels of the group 2 as a correction coefficient.

Similarly, the output of the analog-digital converter of the top master channel and an output of the analog-digital converter of the master channel of the group N are input to the inter-group correction coefficient search portion 309, and the inter-group correction coefficient search portion 309 searches for a mismatch amount of a circuit characteristic of the group N relative to the group 1 on the basis of a difference between both of the outputs. The obtained search value is supplied from the inter-group correction coefficient search portion 309 to the inter-group correction portions 310 and 311 of the respective slave channels of the group N as a correction coefficient. In addition, in the group 3 to the group N-1, the above-described inter-group correction coefficient search is also made. Further, the mismatch amount of the circuit characteristic is a mismatch amount in gain, DC offset voltage, frequency bandwidth, sampling timing, or the like of the other groups relative to the group 1.

Next, transmission and reception operations will be described. During a transmission period, the switches 502, 504, 507, 509, 512 and 514 are turned on, and thus a high voltage pulse or a high voltage analog signal generated by the transmission circuit of the slave channel of each group is applied to each piezoelectric element. The piezoelectric element converts the applied high voltage into vibration due to a piezoelectric effect. The piezoelectric element is pressed to a body surface of a subject (a human body which undergoes ultrasonic diagnosis), and thus the vibration propagates through the body via the body surface as ultrasonic waves. The above description relates to the transmission operation.

The ultrasonic waves which propagate through the body are reflected in a complicated manner by the organs of a living body (which includes human and non-human bodies) or a human body, and are then received by each piezoelectric element of the slave channels via the body surface again. The piezoelectric element converts the received reflected waves of the ultrasonic waves into an electric signal due to the piezoelectric effect. During the reception period, the switches 501, 506, 511, 503, 505, 508, 510, 513 and 515 are turned on, and the switches 502, 504, 507, 509, 512, 514, 516, 517, 518, 519, 520, 521, 522, 523 and 524 are turned off. The received signal which is converted into the electric signal by the piezoelectric element of each slave channel is input to the amplifier so as to undergo signal amplification, and is then converted from an analog signal to a digital signal by the subsequent analog-digital converter.

In addition, in each group, intra-group digital correction is performed as follows. In other words, in the slave channel 1 of the group 1, the intra-group correction portion 109 performs correction through a digital calculation process. A correction coefficient used for the correction is the correction coefficient which is searched for and stored in the intra-group correction portion 109 in the above-described intra-group correction coefficient search operation period. In addition, in the slave channel M-1 of the group 1, the intra-group correction portion 110 performs correction through a digital calculation process. A correction coefficient used for the correction is the correction coefficient which is searched for and stored in the intra-group correction portion 110 in the above-described intra-group correction coefficient search operation period.

Similarly, in the slave channel 1 of the group 2, the intra-group correction portion 212 performs correction through a digital calculation process. A correction coefficient used for the correction is the correction coefficient which is searched for and stored in the intra-group correction portion 212 in the above-described intra-group correction coefficient search operation period. In addition, in the slave channel M-1 of the group 2, the intra-group correction portion 213 performs correction through a digital calculation process. A correction coefficient used for the correction is the correction coefficient which is searched for and stored in the intra-group correction portion 213 in the above-described intra-group correction coefficient search operation period.

Similarly, in the slave channel 1 of the group N, the intra-group correction portion 312 performs correction through a digital calculation process. A correction coefficient used for the correction is the correction coefficient which is searched for and stored in the intra-group correction portion 312 in the above-described intra-group correction coefficient search operation period. In addition, in the slave channel M-1 of the group N, the intra-group correction portion 313 performs correction through a digital calculation process. A correction coefficient used for the correction is the correction coefficient which is searched for and stored in the intra-group correction portion 313 in the above-described intra-group correction coefficient search operation period.

In the slave channels included in the groups other than the group 1, inter-group digital correction is performed as follows. In other words, as described above, the signal corrected by the intra-group correction portion is further corrected by the subsequent inter-group correction portion through a digital calculation process. In a case of the inter-group correction portion of each slave channel of the group 2, a correction coefficient used for the correction is supplied from the inter-group correction coefficient search portion 209 through the inter-group correction coefficient search operation. In addition, in a case of the inter-group correction portion of each slave channel of the group N, a correction coefficient used for the correction is supplied from the inter-group correction coefficient search portion 309 through the inter-group correction coefficient search operation.

The various mismatches are caused by the following. In other words, power consumption increases with the advance of multichannels, and thus temperature fluctuation occurs due to heat generation. In addition, the power supply voltage also fluctuates due to the temperature fluctuation. Due to the temperature fluctuation, a threshold voltage or mobility of the amplifier of each channel or a MOS transistor forming the analog-digital converter fluctuates. As a result of the fluctuation and the power supply voltage fluctuation, a gain, a DC offset voltage, and a frequency bandwidth of an amplifier or an analog-digital converter fluctuate.

In addition, the delay time of a clock buffer which supplies a sampling clock to the analog-digital converter also fluctuates, and thus sampling timing of the analog-digital converter also fluctuates. The way in which the temperature fluctuation or the power supply voltage fluctuation occurs may differ depending on each location in a module or a chip storing multichannels. However, as described above, the channels which have a short distance therebetween are grouped so as to be included in the same group, and thus it can be expected that the way in which the temperature fluctuation or the power supply voltage fluctuation occurs will be uniform in all of the channels included in the same group.

The above-described inter-group correction coefficient search operation is continuously performed at all times including the reception period. The top master channel or the master channels of the group 2 and the subsequent groups are not required to receive ultrasonic signals, and may thus be used only for the inter-group correction coefficient search operation even during the reception period. For this reason, during the reception period, when each slave channel performs a reception process of the ultrasonic signal, the search for an inter-group correction coefficient is continuously made in each group. Temperatures and power supply voltages in the same group can be regarded to be uniform, and thus an inter-group correction coefficient of each group is effective for correction of all of the slave channels included in the group. In addition, an inter-group correction coefficient of each group is continuously searched for even during the reception period and can thus track a temperature fluctuation or a power supply voltage fluctuation.

As causes of the various mismatches, there are manufacturing variations in addition to the temperature fluctuation or the power supply voltage fluctuation. The variations include variations in a threshold value, a gate length and a gate width of a MOS transistor, a variation in a resistance value of a resistive element, a variation in a capacitance value of a capacitive element, variations in wiring resistance and wiring capacitance, and the like. Due to these variations, gains, DC offset voltages, and frequency bandwidths of the amplifier and the analog-digital converter vary.

In addition, sampling timing of the analog-digital converter also varies. Since it is considered that temperature fluctuations and power supply voltage fluctuations of the respective channels (the master channel and the slave channels) included in the same group are regarded to be substantially at the same level, a mismatch of a circuit characteristic between the channels in the same group is caused by the above-described manufacturing variations. The intra-group correction is aimed at correcting the circuit characteristic mismatch in the group, caused by the manufacturing variations.

In order to perform such correction, as described above, in the intra-group correction coefficient search operation period, a common intra-group correction signal is applied to the master channel and each slave channel in the same group, a circuit characteristic mismatch of each slave channel relative to the master channel is searched for as a correction coefficient, and the correction is performed by using the correction coefficient during the reception period. Strictly speaking, the circuit characteristic mismatch in the group caused by the manufacturing variations changes depending on temperature or power supply voltage, but may be regarded to be approximately constant regardless of the temperature or the power supply voltage. Therefore, if an intra-group correction coefficient is searched for in advance with any period earlier than the reception period as the intra-group correction coefficient search period, a correction coefficient obtained at that time may still be effective even during the reception period even if temperatures or power supply voltages differ between the intra-group correction coefficient search operation period and the reception period.

As mentioned above, during the reception period, even in a case where there are manufacturing variations, a characteristic mismatch between the channels can be stably removed through combination between the inter-group digital correction and the intra-group digital correction, and thus it is possible to minimize the occurrence of an artifact in an image.

The above description relates to the Example of the ultrasonic diagnostic apparatus, but the same configuration is employed in a case of a sonar, and thus the same embodiment of the present invention is possible. In addition, medical diagnostic apparatuses such as an X-ray CT apparatus, a PET, and an SPECT are also systems which receive multichannel signals as described above, and the same embodiment of the present invention is possible by omitting the transmission circuit and portions which perform a transmission operation from the present example and by replacing each piezoelectric element with a photodiode for receiving an X-ray signal or a gamma-ray signal.

Example 3

In the present example, with reference to FIG. 3, a description will be made of operations of the intra-group correction portions 109, 110, 212, 213, 312, 313 in Example 2.

An output of each analog-digital converter of each slave channel is input to a multiplier 601. In addition, an output of a gain correction coefficient search portion 600 is a gain correction coefficient value, and is also input to the multiplier 601. Both outputs are multiplied by each other in the multiplier 601, and an output of the multiplier 601 is input to a subtractor 602. In addition, an output of a DC offset correction coefficient search portion 604 is a DC offset correction coefficient value, and is also input to the subtractor 602. In the subtractor 602, the DC offset correction coefficient value is subtracted from the output of the multiplier 601, and thus an intra-group corrected output is obtained.

Simultaneously, the intra-group corrected output is input to a subtractor 603. An output of the analog-digital converter of the master channel which is included in the same group as that including the corresponding slave channel is also input to the subtractor 603. In the subtractor 603, the output of the analog-digital converter of the master channel is subtracted from the intra-group corrected output, and the subtraction result is obtained as an "error". The error is input to the gain correction coefficient search portion 600. An output of the analog-digital converter of the corresponding slave channel is also input to the gain correction coefficient search portion 600.

The gain correction coefficient search portion 600 searches for the gain correction coefficient value on the basis of the error and the output of the analog-digital converter of the slave channel in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 601.

In addition, the error is also input to the DC offset correction coefficient search portion 604. The DC offset correction coefficient search portion 604 searches for the DC offset correction coefficient value on the basis of the error in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the subtractor 602.

The gain correction coefficient value is a value corresponding to a gain mismatch of the corresponding slave channel relative to the master channel, and is multiplied by a signal in the multiplier 601 so that the gain mismatch is digitally compensated for. In addition, the DC offset correction coefficient value is a value corresponding to a DC offset mismatch of the corresponding slave channel relative to the master channel, and is subtracted from the signal in the subtractor 602 so that the DC offset mismatch is digitally compensated for.

The above-described operation is performed in the intra-group correction coefficient search operation period earlier than the reception period, and the gain correction coefficient value and the DC offset correction coefficient value converge on true values after a specific time has elapsed in the same period. The convergence value of the gain correction coefficient value is stored in the gain correction coefficient search portion 600 as it is even after the same period ends, and is used for the intra-group correction during the reception period.

Similarly, the convergence value of the DC offset correction coefficient value is stored in the DC offset correction coefficient search portion 604 as it is even after the same period ends, and is used for the intra-group correction during the reception period. The intra-group correction during the reception period is performed by using the configuration illustrated in FIG. 3, but a correction coefficient value is not searched for, and the correction is performed through calculation in the multiplier 601 and the subtractor 602 by using the gain correction coefficient value and the DC offset correction coefficient value stored as described above.

Example 4

In the present example, operations of the inter-group correction coefficient search portions 209 and 309 in Example 1 or Example 2 will be described with reference to FIG. 4.

An output of the analog-digital converter of each master channel of the group 2 to the group N is input to the multiplier 601. In addition, an output of the gain correction coefficient search portion 600 is a gain correction coefficient value, and is also input to the multiplier 601. Both outputs are multiplied by each other in the multiplier 601, and an output of the multiplier 601 is input to the subtractor 602.

In addition, an output of the DC offset correction coefficient search portion 604 is a DC offset correction coefficient value, and is also input to the subtractor 602. In the subtractor 602, the DC offset correction coefficient value is subtracted from the output of the multiplier 601, and thus the subtraction result is input to the subtractor 603. An output of the analog-digital converter of the master channel (top master channel) of the group 1 is also input to the subtractor 603. In the subtractor 603, the output of the analog-digital converter of the top master channel is subtracted from the above-described subtraction result, and the subtraction result is obtained as an "error". The error is input to the gain correction coefficient search portion 600. An output of the analog-digital converter of the corresponding master channel is also input to the gain correction coefficient search portion 600.

The gain correction coefficient search portion 600 searches for the gain correction coefficient value on the basis of the error and the output of the analog-digital converter of the corresponding master channel in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 601.

In addition, the error is also input to the DC offset correction coefficient search portion 604. The DC offset correction coefficient search portion 604 searches for the DC offset correction coefficient value on the basis of the error in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the subtractor 602.

The gain correction coefficient value is a value corresponding to a gain mismatch of the corresponding master channel relative to the top master channel, and is multiplied by a signal in the multiplier 601 so that the gain mismatch is digitally compensated for. In addition, the DC offset correction coefficient value is a value corresponding to a DC offset mismatch of the corresponding master channel relative to the top master channel, and is subtracted from the signal in the subtractor 602 so that the DC offset mismatch is digitally compensated for.

During the reception period, the correction coefficient value which is obtained as a result of the above-described operation being continuously performed is continuously supplied to the inter-group correction portion of each slave channel in the group including the corresponding master channel as in Examples 1 and 2, and correction is performed in the inter-group correction portion by using the correction coefficient value. Since the correction coefficient value can track a temperature fluctuation or a power supply voltage fluctuation during the reception period, a characteristic mismatch between the channels can be stably removed and thus it is possible to minimize the occurrence of an artifact in an image during the reception period.

In addition, each inter-group correction portion is constituted only by the multiplier 601 and the subtractor 602 of FIG. 4. The multiplier 601 performs multiplication by the gain correction coefficient value which is output from the inter-group correction coefficient search portion so as to obtain a multiplication output. Further, the subtractor 602 subtracts the DC offset correction coefficient value which is output from the inter-group correction coefficient search portion, from the multiplication output. An output of the subtractor 602 becomes an output of the inter-group correction portion.

Example 5

In the present example, with reference to FIG. 5, a description will be made of operations of the intra-group correction portions 109, 110, 212, 213, 312, 313 in Example 2. In the present example, a sampling timing correction coefficient search function is added to Example 3.

An output of each analog-digital converter of each slave channel is input to the multiplier 601. In addition, an output of a gain correction coefficient search portion 600 is a gain correction coefficient value, and is also input to the multiplier 601. Both outputs are multiplied by each other in the multiplier 601, and an output of the multiplier 601 is input to the subtractor 602. In addition, an output of a DC offset correction coefficient search portion 604 is a DC offset correction coefficient value, and is also input to the subtractor 602. In the subtractor 602, the DC offset correction coefficient value is subtracted from the output of the multiplier 601, and the subtraction result is input to a differentiator 607 and a subtractor 605. A "sampling timing correction term value" which is an output of a multiplier 606 is also input to the subtractor 605. The subtractor 605 subtracts the sampling timing correction term value from the output of the subtractor 602, and the subtraction result becomes an intra-group corrected output.

Simultaneously, the intra-group corrected output is input to a subtractor 603. An output of the analog-digital converter of the master channel which is included in the same group as that including the corresponding slave channel is also input to the subtractor 603. In the subtractor 603, the output of the analog-digital converter of the master channel is subtracted from the intra-group corrected output, and the subtraction result is obtained as an "error". The error is input to the gain correction coefficient search portion 600. An output of the analog-digital converter of the corresponding slave channel is also input to the gain correction coefficient search portion 600.

The gain correction coefficient search portion 600 searches for the gain correction coefficient value on the basis of the error and the output of the analog-digital converter of the slave channel in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 601.

In addition, the error is also input to the DC offset correction coefficient search portion 604. The DC offset correction coefficient search portion 604 searches for the DC offset correction coefficient value on the basis of the error in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the subtractor 602.

Further, the error is also input to a sampling timing correction coefficient search portion 608. An output (that is, a differential value of the signal) of a differentiator 607 is also input to the sampling timing correction coefficient search portion 608. The sampling timing correction coefficient search portion 608 searches for a sampling timing correction coefficient value on the basis of the error and the output of the differentiator 607 in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 606. The multiplier 606 multiplies the output of the differentiator 607 by the sampling timing correction coefficient value, and outputs the multiplication result to the subtractor 605 as the sampling timing correction term value.

The gain correction coefficient value is a value corresponding to a gain mismatch of the corresponding slave channel relative to the master channel, and is multiplied by a signal in the multiplier 601 so that the gain mismatch is digitally compensated for. In addition, the DC offset correction coefficient value is a value corresponding to a DC offset mismatch of the corresponding slave channel relative to the master channel, and is subtracted from the signal in the subtractor 602 so that the DC offset mismatch is digitally compensated for. Further, the sampling timing correction coefficient value is a value corresponding to a sampling timing mismatch of the corresponding slave channel relative to the master channel, and is multiplied by the differential value of the signal in the multiplier 606 so that a sampling error voltage (sampling timing correction term value) of the analog-digital converter caused by the sampling timing mismatch is obtained and is subtracted in the subtractor 605. Therefore, the sampling timing mismatch is digitally compensated for.

The above-described operation is performed in the intra-group correction coefficient search operation period earlier than the reception period, and the gain correction coefficient value, the DC offset correction coefficient value, and the sampling timing correction coefficient value converge on true values after a specific time has elapsed in the same period. The convergence value of the gain correction coefficient value is stored in the gain correction coefficient search portion 600 as it is even after the same period ends, and is used for the intra-group correction during the reception period. Similarly, the convergence value of the DC offset correction coefficient value is stored in the DC offset correction coefficient search portion 604 as it is even after the same period ends, and is used for the intra-group correction during the reception period. Similarly, the convergence value of the sampling timing correction coefficient value is stored in the sampling timing correction coefficient search portion 608 as it is even after the same period ends, and is used for the intra-group correction during the reception period.

Figure 5:
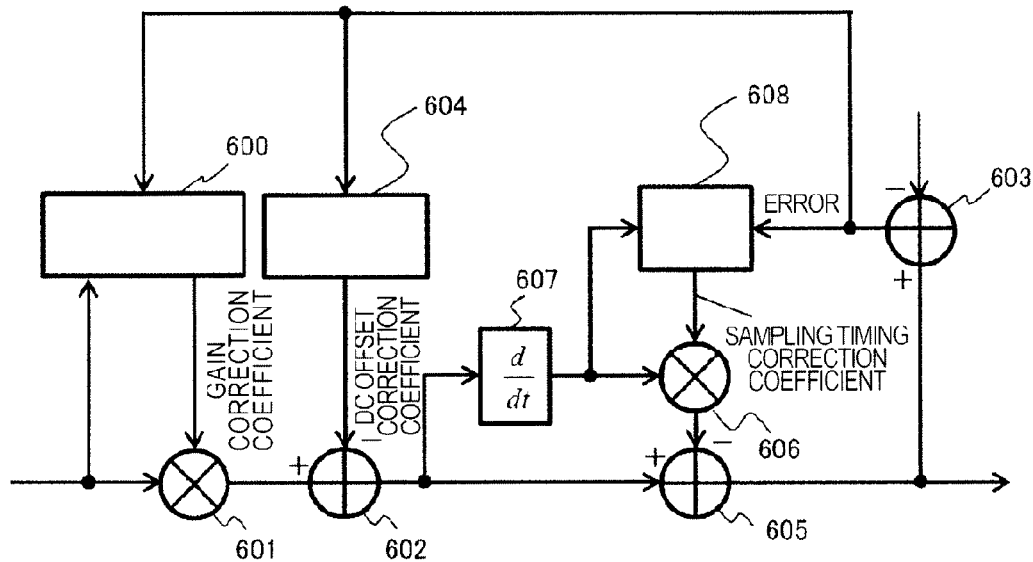
FIG. 5 is a diagram illustrating Example 5 of the present invention.

The intra-group correction during the reception period is performed by using the configuration illustrated in FIG. 5, but a correction coefficient value is not searched for, and the correction is performed through calculation in the multiplier 601, the subtractor 602, the differentiator 607, the multiplier 606, and the subtractor 605 by using the gain correction coefficient value, the DC offset correction coefficient value, and the sampling timing correction coefficient value stored as described above.

In addition, the above-described sampling timing correction coefficient value automatically includes influences of effective sampling timing deviations due to a frequency bandwidth mismatch between the amplifiers or the analog-digital converters in addition to a sampling timing mismatch amount between the analog-digital converters. Therefore, with the present configuration, not only the sampling timing mismatch between the analog-digital converters but also the frequency bandwidth mismatch between the amplifiers or the analog-digital converters can be corrected.

Example 6

In the present example, operations of the inter-group correction coefficient search portions 209 and 309 in Example 1 or Example 2 will be described with reference to FIG. 6. In the present example, a sampling timing correction coefficient search function is added to Example 4.

An output of the analog-digital converter of each master channel of the group 2 to the group N is input to the multiplier 601. In addition, an output of the gain correction coefficient search portion 600 is a gain correction coefficient value, and is also input to the multiplier 601. Both outputs are multiplied by each other in the multiplier 601, and an output of the multiplier 601 is input to the subtractor 602.

In addition, an output of the DC offset correction coefficient search portion 604 is a DC offset correction coefficient value, and is also input to the subtractor 602. In the subtractor 602, the DC offset correction coefficient value is subtracted from the output of the multiplier 601, and thus the subtraction result is input to the differentiator 607 and the subtractor 605. A "sampling timing correction term value" which is an output of a multiplier 606 is also input to the subtractor 605. The subtractor 605 subtracts the sampling timing correction term value from the output of the subtractor 602, and the subtraction result is input to the subtractor 603.

An output of the analog-digital converter of the master channel (top master channel) of the group 1 is also input to the subtractor 603. In the subtractor 603, the output of the analog-digital converter of the top master channel is subtracted from the above-described subtraction result, and the subtraction result is obtained as an "error". The error is input to the gain correction coefficient search portion 600. An output of the analog-digital converter of the corresponding master channel is also input to the gain correction coefficient search portion 600.

The gain correction coefficient search portion 600 searches for the gain correction coefficient value on the basis of the error and the output of the analog-digital converter of the corresponding master channel in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 601.

In addition, the error is also input to the DC offset correction coefficient search portion 604. The DC offset correction coefficient search portion 604 searches for the DC offset correction coefficient value on the basis of the error in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the subtractor 602.

Further, the error is also input to a sampling timing correction coefficient search portion 608. An output (that is, a differential value of the signal) of the differentiator 607 is also input to the sampling timing correction coefficient search portion 608. The sampling timing correction coefficient search portion 608 searches for a sampling timing correction coefficient value on the basis of the error and the output of the differentiator 607 in the same manner as in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, and supplies the coefficient value to the multiplier 606. The multiplier 606 multiplies the output of the differentiator 607 by the sampling timing correction coefficient value, and outputs the multiplication result to the subtractor 605 as the sampling timing correction term value.

The gain correction coefficient value is a value corresponding to a gain mismatch of the corresponding master channel relative to the top master channel, and is multiplied by a signal in the multiplier 601 so that the gain mismatch is digitally compensated for. In addition, the DC offset correction coefficient value is a value corresponding to a DC offset mismatch of the corresponding master channel relative to the top master channel, and is subtracted from the signal in the subtractor 602 so that the DC offset mismatch is digitally compensated for.

Further, the sampling timing correction coefficient value is a value corresponding to a sampling timing mismatch of the corresponding master channel relative to the top master channel, and is multiplied by the differential value of the signal in the multiplier 606 so that a sampling error voltage (sampling timing correction term value) of the analog-digital converter caused by the sampling timing mismatch is obtained and is subtracted in the subtractor 605. Therefore, the sampling timing mismatch is digitally compensated for. During the reception period, the correction coefficient value which is obtained as a result of the above-described operation being continuously performed is continuously supplied to the inter-group correction portion of each slave channel in the group including the corresponding master channel as in Examples 1 and 2, and correction is performed in the inter-group correction portion by using the correction coefficient value. Since the correction coefficient value can track a temperature fluctuation or a power supply voltage fluctuation during the reception period, a characteristic mismatch between the channels can be stably removed and thus it is possible to minimize the occurrence of an artifact in an image during the reception period.

Figure 6:
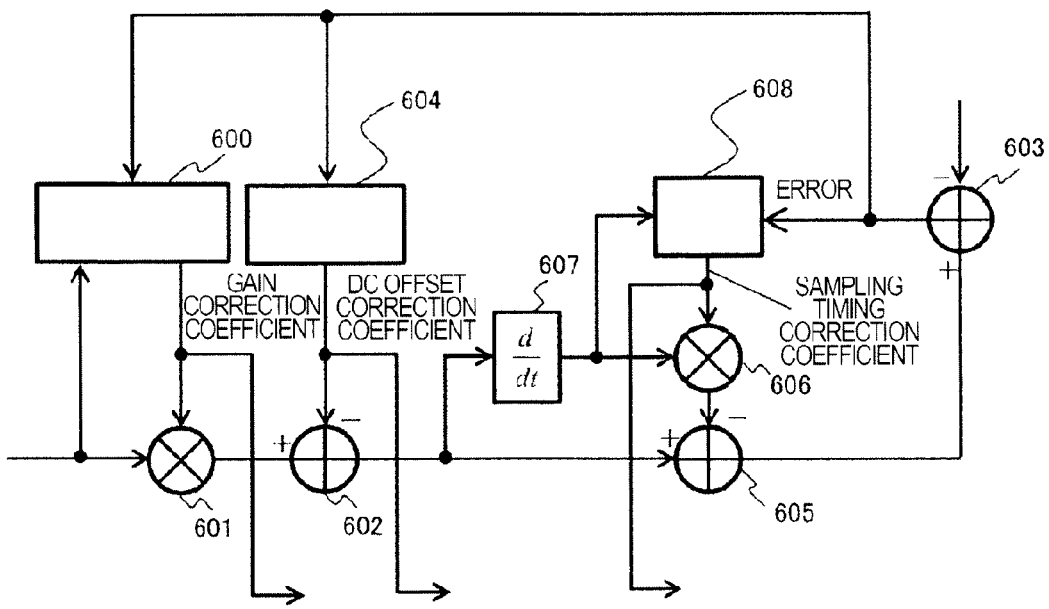
FIG. 6 is a diagram illustrating Example 6 of the present invention.

In addition, each inter-group correction portion is constituted only by the multiplier 601, the subtractor 602, the differentiator 607, the multiplier 606, and the subtractor 605 of FIG. 6. The multiplier 601 performs multiplication by the gain correction coefficient value which is output from the inter-group correction coefficient search portion so as to obtain a multiplication output.

Figure 7:
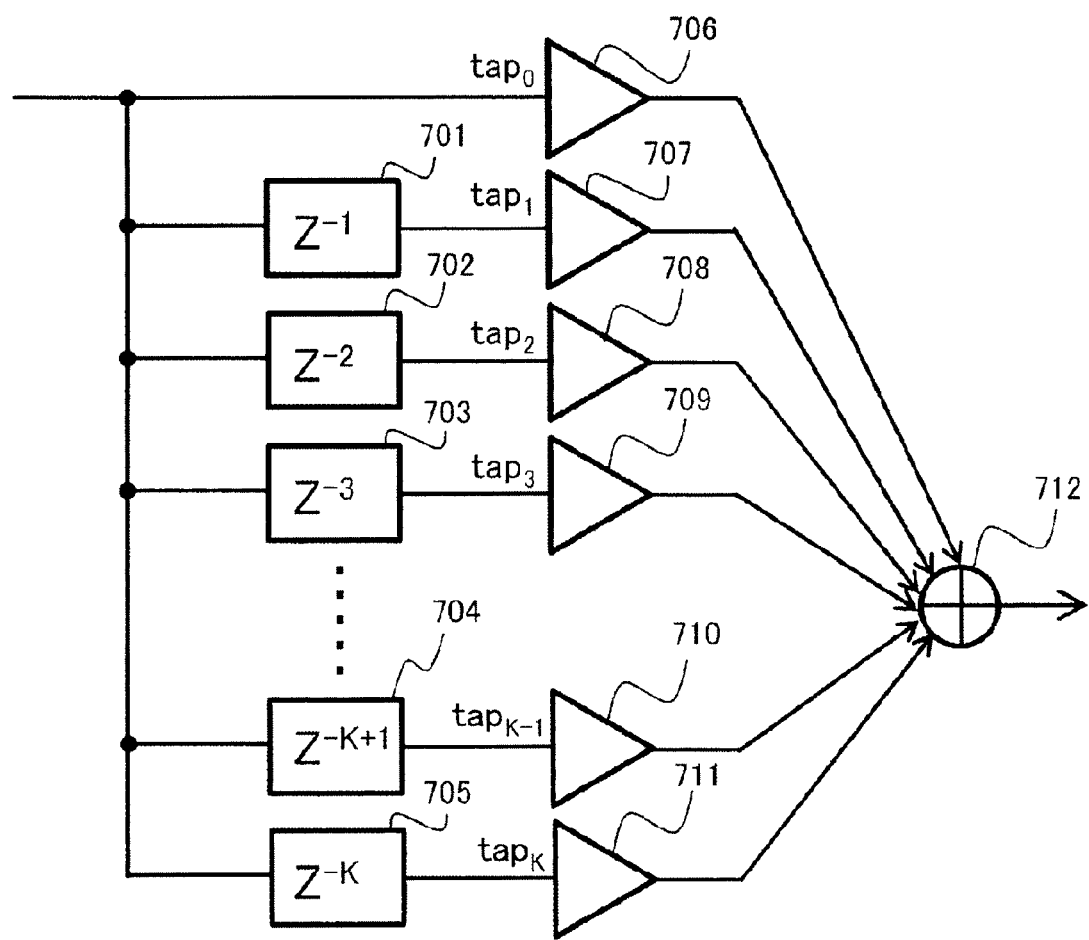
FIG. 7 is a supplementary diagram of Example 6 of the present invention.

Further, the subtractor 602 subtracts the DC offset correction coefficient value which is output from the inter-group correction coefficient search portion, from the multiplication output. The subtraction result is differentiated in the differentiator 607, and the multiplier 606 multiplies the differentiated signal by the sampling timing correction coefficient value which is output from the inter-group correction coefficient search portion. Still further, in the subtractor 605, the multiplication result is subtracted from the subtraction result. An output of the subtractor 605 becomes an output of the inter-group correction portion. In addition, the above-described sampling timing correction coefficient value automatically includes influences of effective sampling timing deviations due to a frequency bandwidth mismatch between the amplifiers or the analog-digital converters in addition to a sampling timing mismatch amount between the analog-digital converters. Therefore, with the present configuration, not only the sampling timing mismatch between the analog-digital converters but also the frequency bandwidth mismatch between the amplifiers or the analog-digital converters can be corrected. The differentiator 607 can be easily implemented by using, for example, a finite impulse response (FIR) digital filter illustrated in FIG. 7. A configuration and an operation thereof are as disclosed in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009.

A signal is input to a constant multiplier 706, a one-sample delay portion 701, a two-sample delay portion 702, a three-sample delay portion 703, a (K−1)-sample delay portion 704, and a K-sample delay portion 705. Here, K+1 is the number of taps of the FIR filter. Outputs of the delay portions 701, 702, 703, 704 and 705 are respectively input to constant multipliers 707, 708, 709, 710 and 711.

In addition, outputs of the constant multipliers 706, 707, 708, 709, 710 and 711 are input to an adder 712. The adder 712 adds the outputs together so as to output an addition result. The output of the adder 712 is an output of the differentiator 607 which outputs a signal obtained by differentiating the input signal. The constant multipliers 706, 707, 708, 709, 710 and 711 respectively multiply inputs thereof by tap coefficient values $tap_0$, $tap_1$, $tap_2$, $tap_3$, $taP_{K-1}$, and $tap_K$, and respectively output the obtained results. Specifically, a differential transfer function (j·2πf) can be realized with the configuration illustrated in FIG. 7 by using each tap coefficient value shown in Equation (1). In addition, $f_{CLK}$ indicates an operation clock frequency.

Equation 1

$$\begin{cases} tap_{K/2} = 0 \\ tap_{K/2 \pm n} = \mp(-1)^{n+1} \cdot \frac{1}{n} \cdot f_{CLK}\left(1 \le n \le \frac{K}{2}\right) \end{cases} \quad (1)$$

As the number of taps becomes larger, that is, K becomes greater, accuracy of a differential value becomes higher, but the circuit mounting area and the power consumption of the differentiator increase. As disclosed in Takashi Oshima, Tomomi Takahashi and Taizo Yamawaki, "Novel sampling timing background calibration for time-interleaved A/D converters," IEEE 52nd International Midwest Symposium on Circuits and Systems, pp. 361 to 364, August 2009, a value obtained by applying a window function process to the value expressed by Equation (1) is used as each actual tap coefficient value, and thus it is possible to ensure sufficient accuracy of a differential value with several tens of taps.

Example 7

As Example 7 of the present invention, operation timing of each Example described above is illustrated in FIG. 8. The present example is applicable to an ultrasonic diagnostic apparatus and a sonar. In this system, transmission and reception of ultrasonic waves are alternately performed. As illustrated on the top part of FIG. 8, a temperature fluctuation or a power supply voltage fluctuation may occur in each channel in correlation with the transmission and reception operations.

Figure 8:
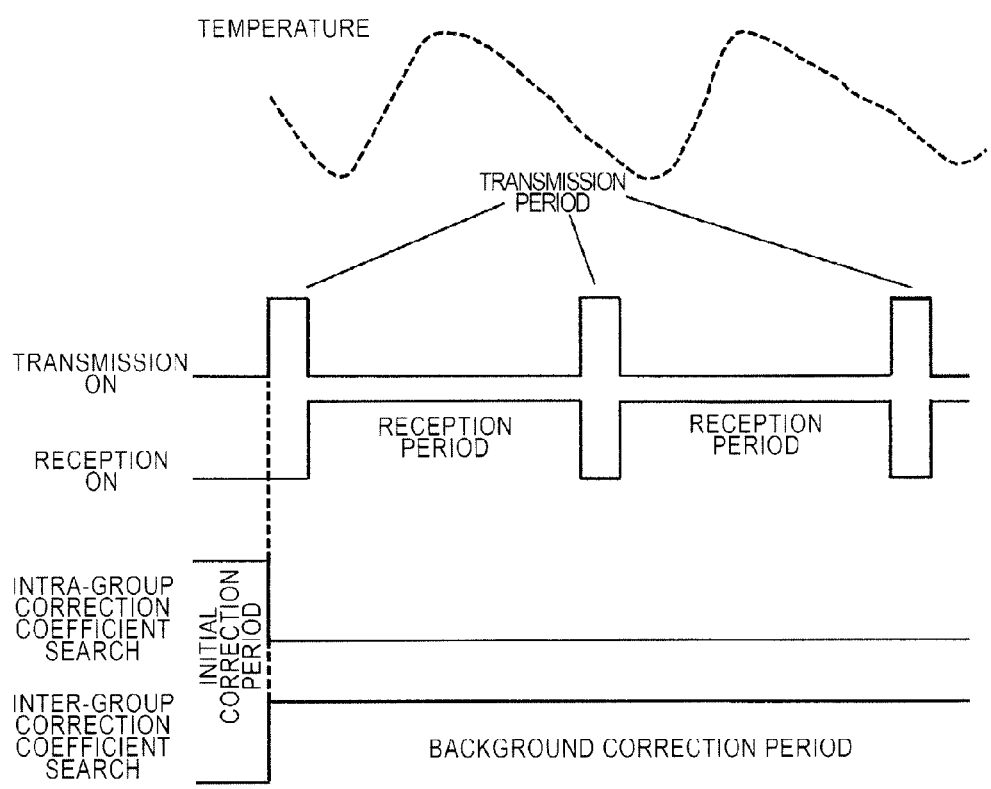
FIG. 8 is a diagram illustrating Example 7 of the present invention.

In FIG. 8, the ultrasonic waves are transmitted in a period in which a "transmission On" waveform has a high voltage, and the ultrasonic waves are received in a period in which a "reception On" waveform has a high voltage. Configurations and operations of the respective circuit portions in the transmission period and the reception period are as described in Example 1, 2 or the like.

In a period in which an "intra-group correction coefficient search" waveform of FIG. 8 has a high voltage, the intra-group correction coefficient search operation described in Example 2 or the like is performed. In the present example, the intra-group correction coefficient search operation is performed only in an "initial correction period" which is a period before the transmission and reception of the ultrasonic waves are started. In addition, the inter-group correction coefficient search operation described in Example 1, 2, or the like is continuously performed in the background of the transmission and reception operations after the intra-group correction coefficient search operation is finished.

The intra-group correction coefficient search operation is performed only in the initial correction period, and thus there is an advantage in that an operation sequence can be simplified. As this initial correction period, for example, a starting time of a device system may be set.

During the reception period, even in a case where there are manufacturing variations, a characteristic mismatch between the channels can be stably removed through combination between the inter-group digital correction based on the inter-group correction coefficient search operation and the intra-group digital correction based on the intra-group correction coefficient search operation, and thus it is possible to minimize the occurrence of an artifact in an image.

Example 8

Figure 9:
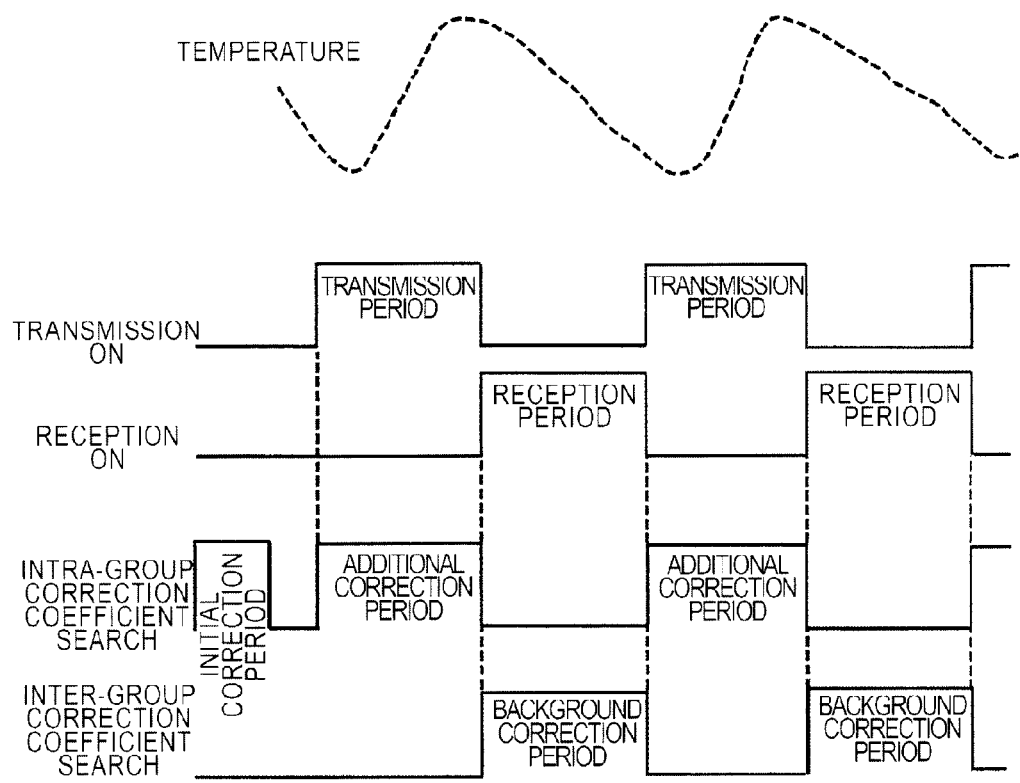
FIG. 9 is a diagram illustrating Example 8 of the present invention.

As Example 8 of the present invention, operation timing of Examples 1 to 6 described above is illustrated in FIG. 9. The present example is applicable to an ultrasonic diagnostic apparatus and a sonar. In this system, transmission and reception of ultrasonic waves are alternately performed. As illustrated on the top part of FIG. 9, a temperature fluctuation or a power supply voltage fluctuation may occur in each channel in correlation with the transmission and reception operations. In FIG. 9, the ultrasonic waves are transmitted in a period in which a "transmission On" waveform has a high voltage, and the ultrasonic waves are received in a period in which a "reception On" waveform has a high voltage. Configurations and operations of the respective circuit portions in the transmission period and the reception period are as described in Example 1, 2 or the like. In a period in which an "intra-group correction coefficient search" waveform of FIG. 9 has a high voltage, the intra-group correction coefficient search operation described in Example 2 or the like is performed. In the present example, the intra-group correction coefficient search operation is performed during the transmission period (indicated as an "additional correction period") in addition to an "initial correction period" which is a period before the transmission and reception of the ultrasonic waves are started. In addition, the inter-group correction coefficient search operation described in Example 1, 2, or the like is continuously performed in the background during the reception period.

Since the intra-group correction coefficient search operation is also performed during the transmission period, each correction coefficient value in a temperature or power supply voltage state right before the reception period is started can be obtained and can thus be used for the intra-group correction during the reception period. Strictly speaking, a circuit characteristic mismatch in the group caused by the manufacturing variations changes depending on a temperature or a power supply voltage, and thus a correction coefficient value is preferably searched for in a state as close to a temperature and a power supply voltage during the reception period as possible.

In the present example, since each intra-group correction coefficient value can be searched for until right before the reception period is started, a circuit characteristic mismatch in a group during the reception period can be corrected with high accuracy by using the obtained correction coefficient value.

During the reception period, even in a case where there are manufacturing variations, a characteristic mismatch between the channels can be stably removed through combination between the inter-group digital correction based on the inter-group correction coefficient search operation and the intra-group digital correction based on the intra-group correction coefficient search operation, and thus it is possible to minimize the occurrence of an artifact in an image.

Example 9

Figure 10:
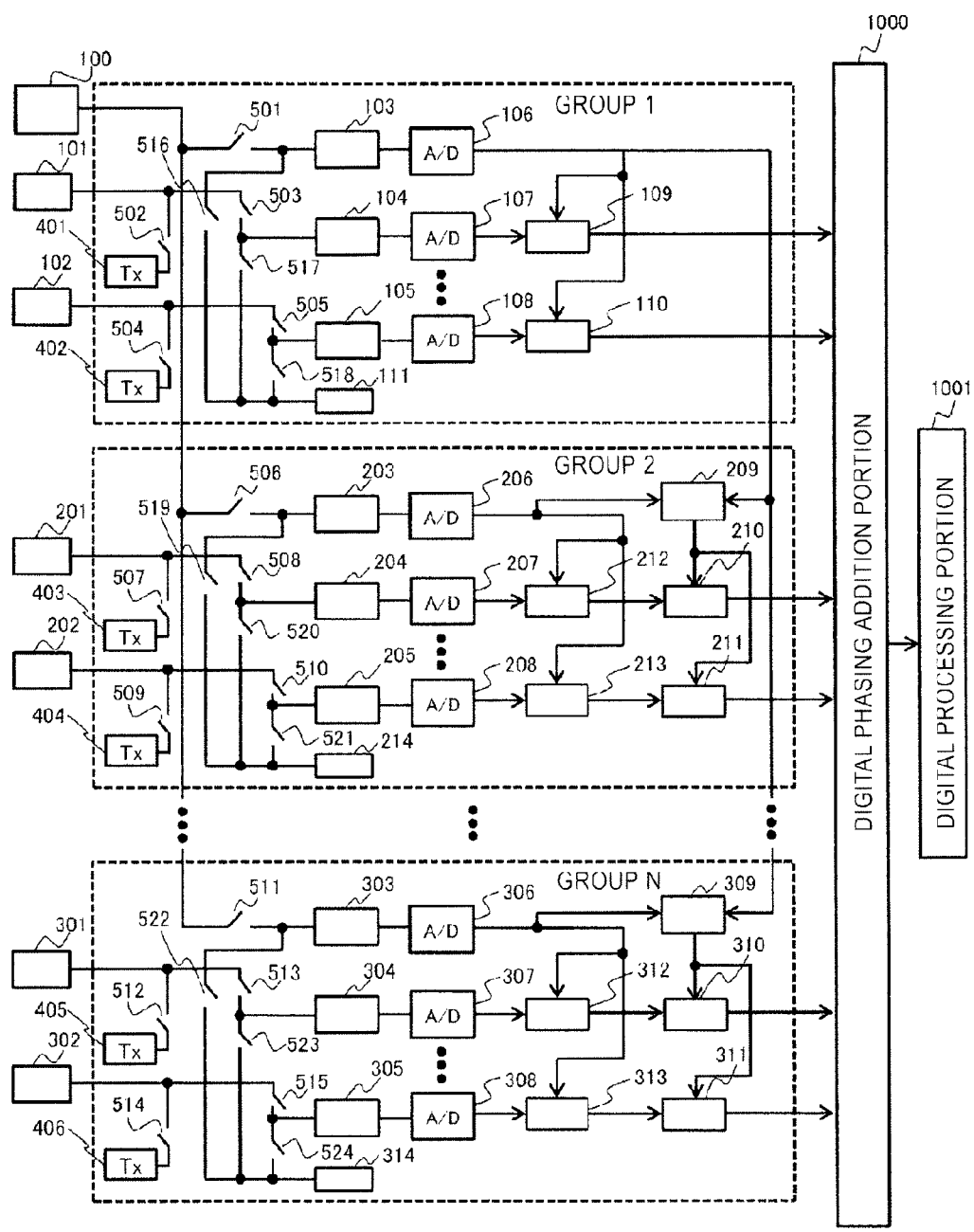
FIG. 10 is a diagram illustrating Example 9 of the present invention.

FIG. 10 illustrates Example 9 of the present invention. The present example is applicable to an ultrasonic diagnostic apparatus and a sonar. In the present example, a digital phasing addition portion and a digital processing portion are additionally connected to the output terminals of the slave channels in Example 2. Consequently, a configuration of the ultrasonic diagnostic apparatus or the sonar is completed. An output of each slave channel is input to a digital phasing addition portion 1000. An output of the digital phasing addition portion 1000 is input to a digital processing portion 1001.

A configuration and an operation thereof are as described in Example 2, and thus a circuit characteristic mismatch between the outputs of the respective slave channels is corrected so that an ideal state occurs in which there is no mismatch in an equivalent manner.

The digital phasing addition portion 1000 delays the outputs of the respective slave channels by predetermined delay amounts through digital calculation, and then adds the delayed signals of the slave channels together. Ultrasonic signals received by the piezoelectric elements 101, 102, 201, 202, 301 and 302 of the respective slave channels are different in delay amounts. Such delay amounts reflect internal structure information of a subject. The delay amount differences are compensated for through the delay process in the digital phasing addition portion 1000 so that phases of signals of the respective slave channels are aligned, and thus it is possible to enhance amplitudes of signals obtained as a result of the addition process.

In a case where a circuit characteristic mismatch between the slave channels is not corrected, the "phasing" operation of the digital phasing addition portion 1000 does not effectively function. For example, if there is a sampling timing mismatch between the slave channels, a value by adding a sampling timing mismatch amount to the predetermined delay amount set in the digital phasing addition portion 1000 becomes a substantial delay amount. Consequently, accuracy of the phasing is reduced.

In the present invention, as described in Example 1, 2, or the like, during the reception period, a characteristic mismatch between the channels can be stably removed so that favorable phasing accuracy can be maintained, and thus it is possible to minimize the occurrence of an artifact in an image.

Example 10

Figure 11:
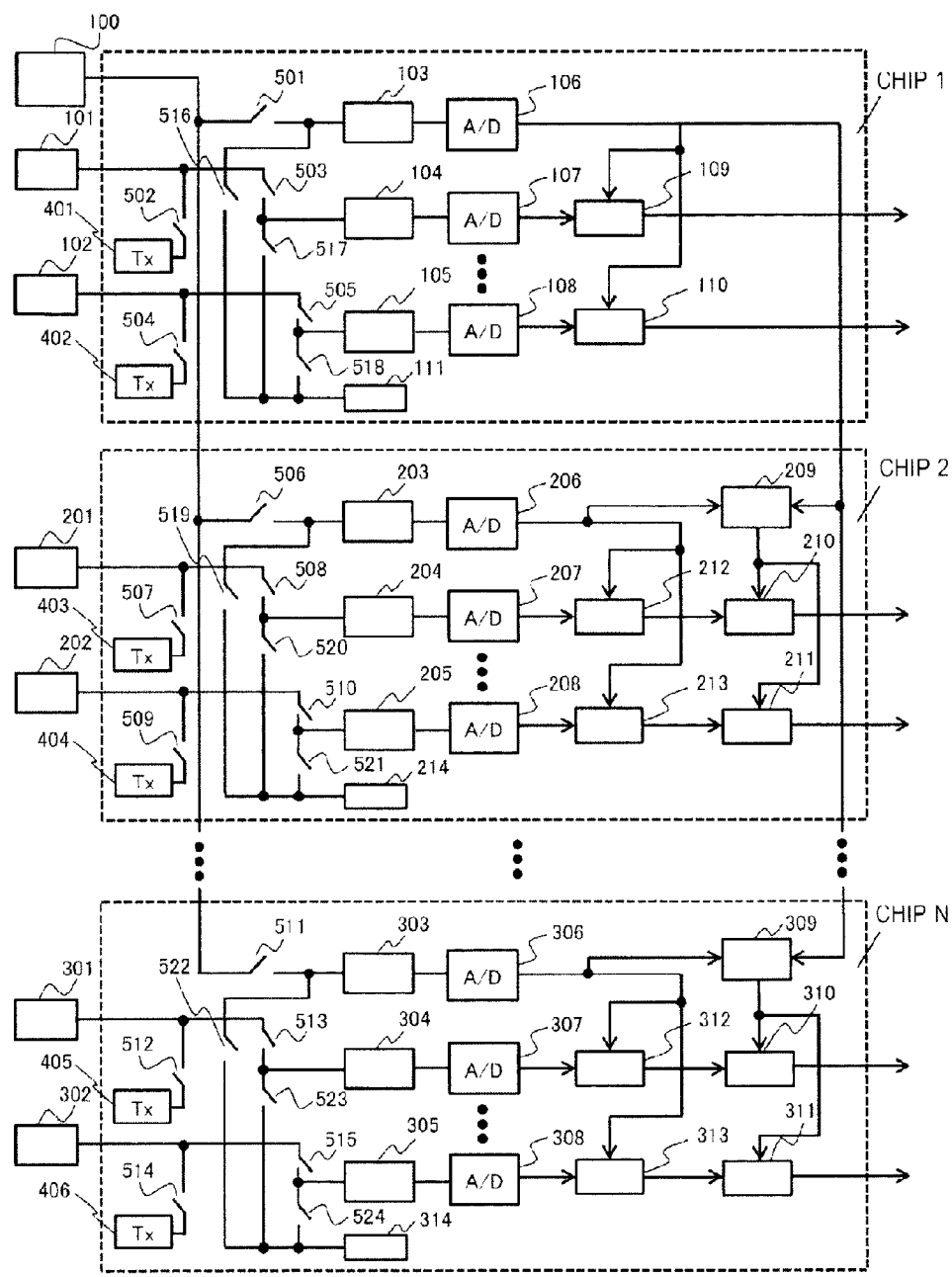
FIG. 11 is a diagram illustrating Example 10 of the present invention.

FIG. 11 illustrates Example 10 of the present invention. The present example shows an example in which the grouping is performed in the chip unit in Example 2.

In a medical diagnostic apparatus such as an ultrasonic diagnostic apparatus or a sonar constituted by N semiconductor chips (ICs), each chip includes a single master channel and (M-1) slave channels, and thus ultrasonic signals (or other types of signals) of a total of N*(M-1) channels can be transmitted and received (or may be received only). In a case where the number M of channels per chip is not large, a chip area or power consumption per chip is relatively small, and thus a temperature or a power supply voltage in the chip can be regarded to be approximately uniform. Therefore, the grouping unit in Example 2 is set to the chip unit, and the respective channels in a chip 1 are allocated to the group 1, the respective channels in a chip 2 are allocated to the group 2, and the respective channels in a chip N are allocated to the group N.

In addition, in a case where the number M of channels per chip is large, a chip area or power consumption per chip is large, it cannot be expected that a temperature or a power supply voltage in the chip is uniform. In this case, a plurality of groups are formed in a single chip. In addition, the channels close to each other at mutual distances may be included in the same group, and thus temperatures and power supply voltages of all the channels included in the same group may be regarded to be uniform, that is, temperature fluctuations and power supply voltage fluctuations may be regarded to be substantially in the same level.

Figure 12:
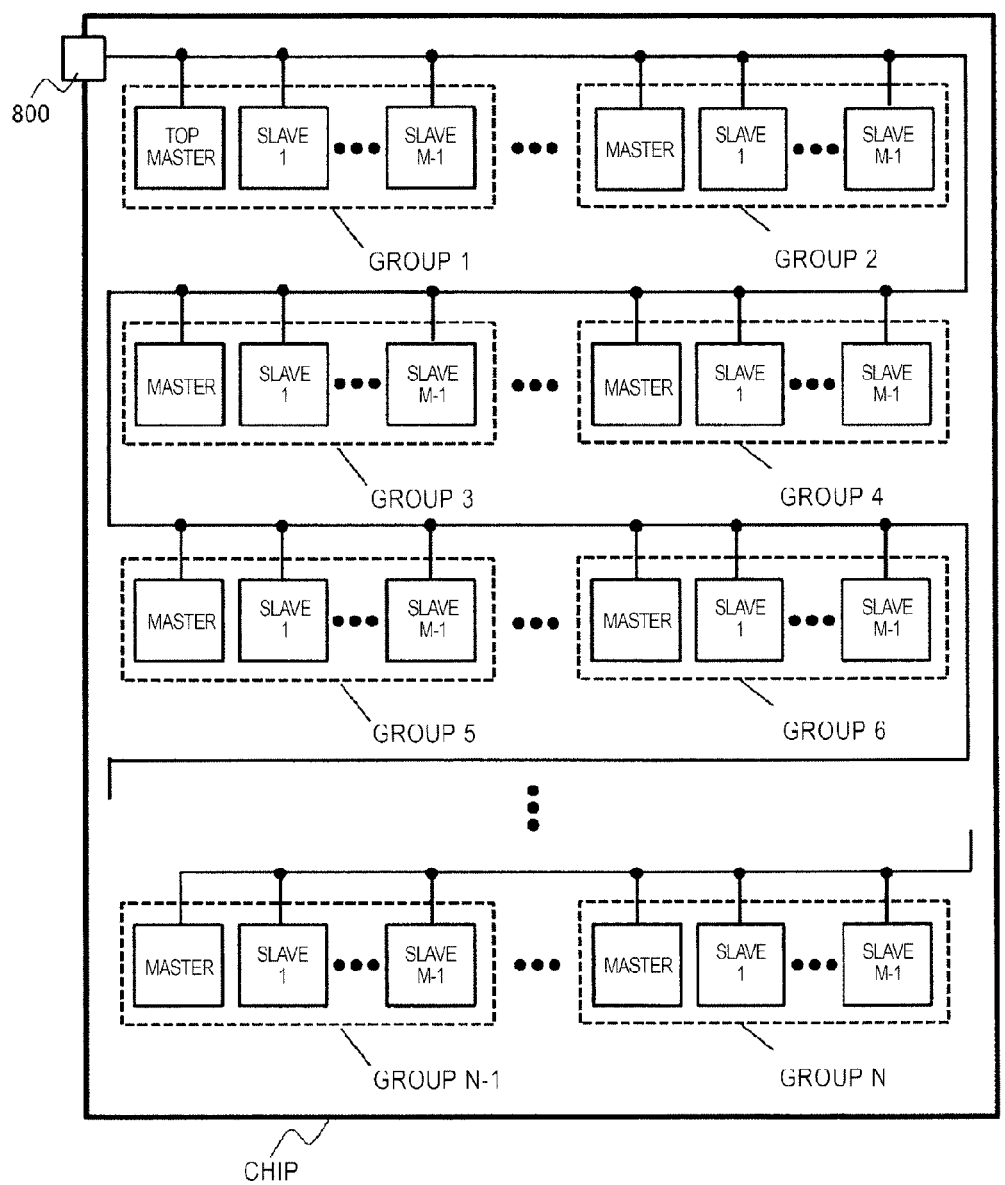
FIG. 12 is a supplementary diagram of Example 10 of the present invention.

In addition, in a case where the number M of channels per chip is large, there is a case where lengths of power supply wirings to the respective channels are greatly different as illustrated in FIG. 12. Particularly, as illustrated in FIG. 12, the case is a case where power is supplied via a single trunk power supply wiring. In order to reduce a chip area, a layout area of the power supply wiring is required to be reduced as much as possible, and thus such a power supply wiring is frequently used. In this case, regarding channels disposed directly near a power supply terminal 800 of the chip, a power supply wiring length to the channels is small. On the contrary, as the channels are disposed farther from the power supply terminal 800 of the chip, a power supply wiring length to the channels is increased.

Therefore, in such a case, as illustrated in FIG. 12, groups are allocated sequentially from the power supply terminal 800 of the chip along the trunk power supply wiring. Consequently, regarding the channels included in the same group, power supply wiring lengths from the power supply terminal 800 of the chip are substantially the same as each other. As a result, since power supply voltage drops of the respective channels caused by the power supply wiring resistance are substantially the same as each other, power supply voltages of the respective channels in the group can be regarded to be uniform. Therefore, the correction described in Example 1, 2, or the like can be applied.

Example 11

Figure 13:
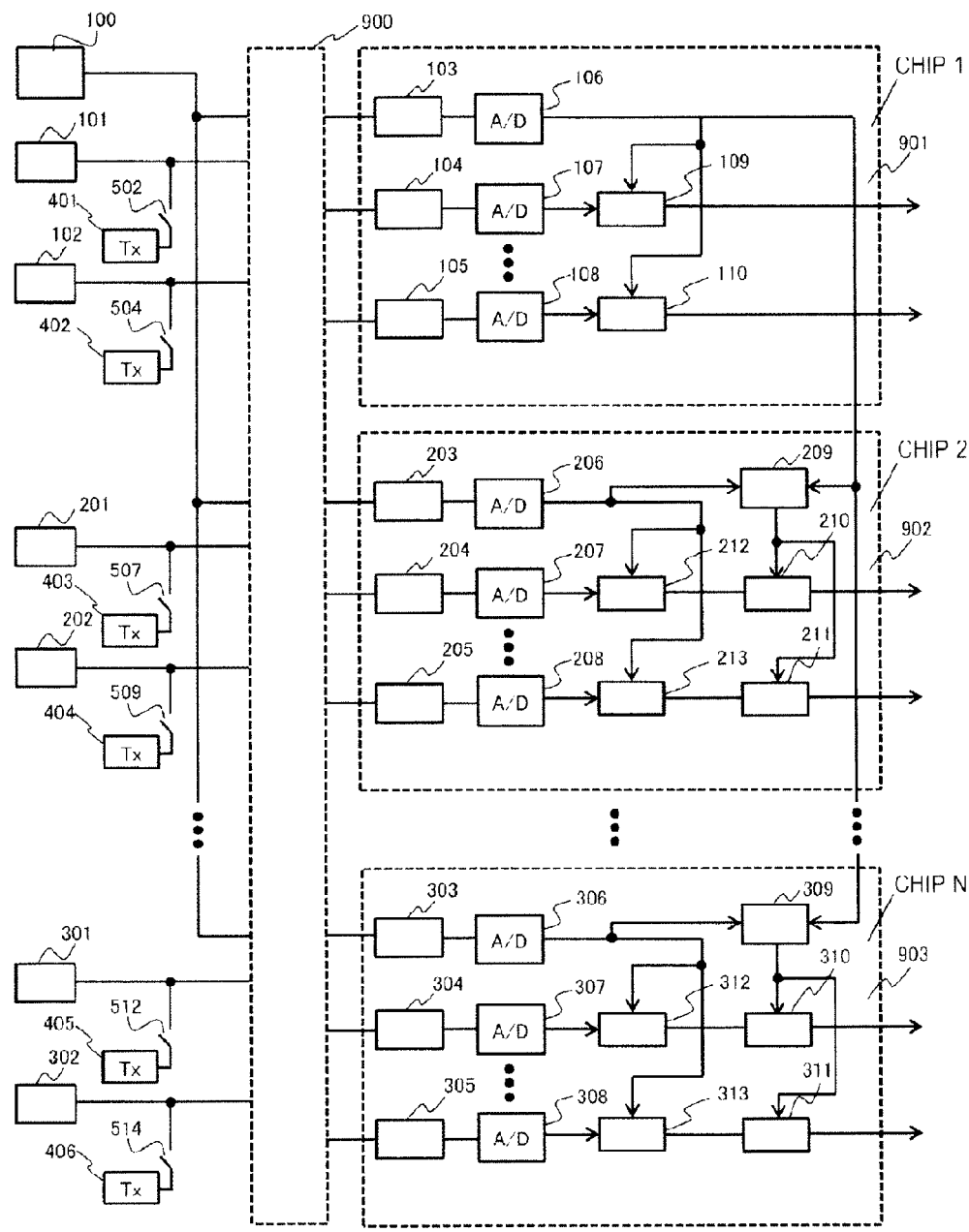
FIG. 13 is a diagram illustrating Example 11 of the present invention.
Figure 14:
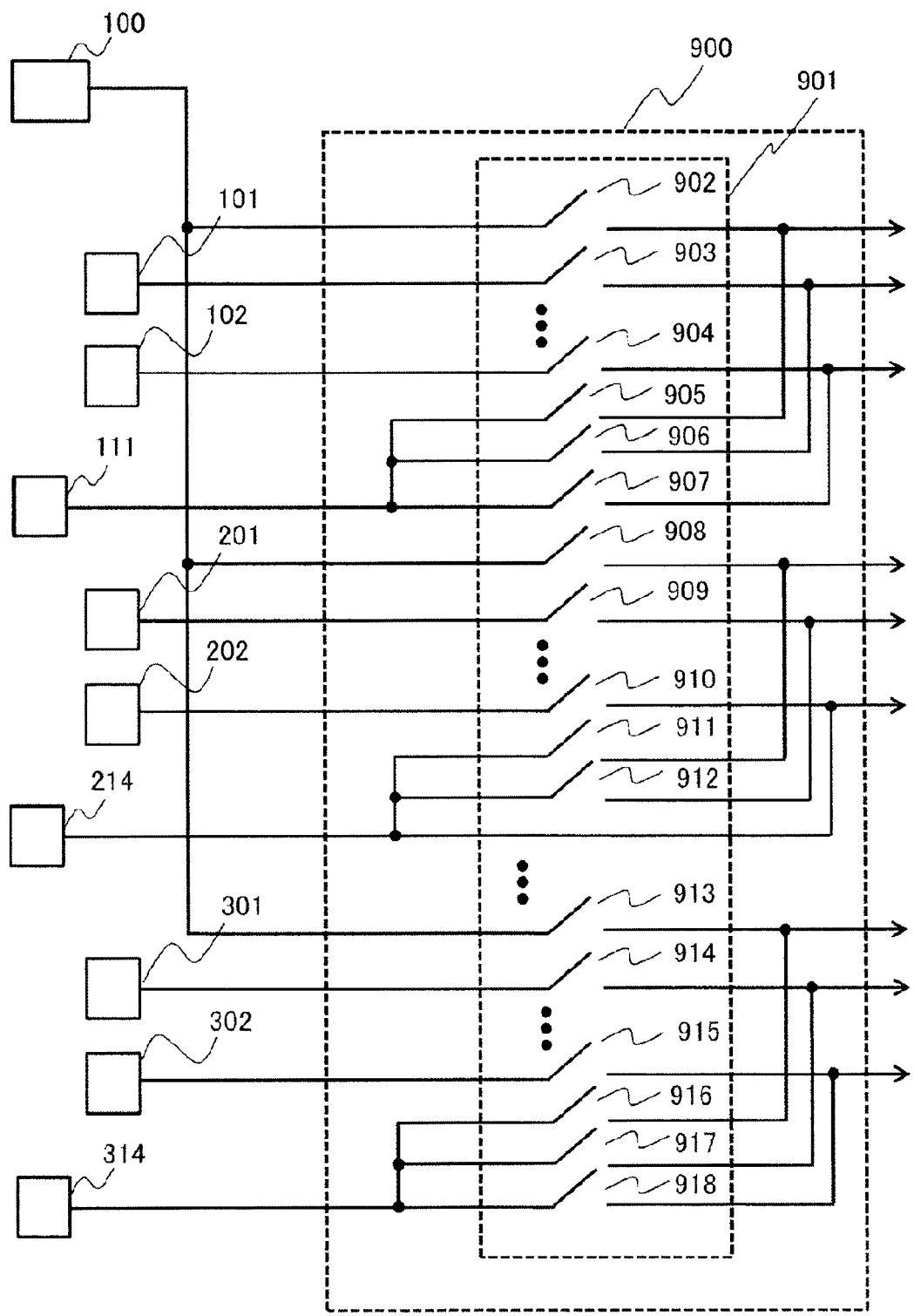
FIG. 14 is a supplementary diagram of Example 11 of the present invention.

Example 11 of the present invention will be described with reference to FIGS. 13 and 14. The present example is an example in which the same configuration as in Example 2 is realized by using a plurality of chips available in the market. In the present example, chips 1 to N include only reception circuits, and transmission circuits (Tx) are mounted in separate chips or separate modules. A multiplexer portion 900 of FIG. 13 has a configuration illustrated in FIG. 14, and includes a multiplexer IC 901. The multiplexer IC 901 is an IC chip in which a plurality of analog switches 902, 903, 904, 905, 906, 907, 908, 909, 910, 911, 912, 913, 914, 915, 916, 917 and 918 are mounted in parallel to each other, and a product available in the market may be used. With the above-described configuration, the same configuration as in Example 2 can be realized by using combination of inexpensive chips available in the market. Each operation is the same as in Example 2.

Each Example described above is an example in which the reception circuit of each channel is formed by the amplifier and the analog-digital converter, but the present invention is also effectively applicable to a case where an analog circuit such as a filter is provided on a pre-stage or a post-stage of the amplifier.

The above-described structure or function of the ultrasonic diagnostic apparatus may be implemented in the main body of the ultrasonic diagnostic apparatus, and may be implemented in a probe (ultrasonic diagnostic probe) which is connected to the main body of the ultrasonic diagnostic apparatus via a cable or in a wireless manner. In addition, the structure or the function thereof may be implemented in both of the main body of the ultrasonic diagnostic apparatus and the ultrasonic diagnostic probe. The present invention is also effectively applicable to all such cases.

Further, in each Example described above, the intra-group correction portion and the inter-group correction portion have been described as separate blocks, but may share calculators. For example, the respective calculators (the multiplier 601, the subtractor 602, the differentiator 607, the multiplier 606, and the subtractor 605) of the intra-group correction portion as illustrated in FIG. 5 may be used instead of the respective corresponding calculators of the inter-group correction portion. In this case, a gain correction coefficient value, a DC offset correction coefficient value, and a sampling timing correction coefficient value obtained by the inter-group correction coefficient search portion are supplied to the intra-group correction portion. The intra-group correction portion adds the respective correction coefficient values supplied from the inter-group correction coefficient search portion to correction coefficient values which are obtained by the intra-group correction portion during an intra-group correction coefficient search operation, and can collectively perform intra-group correction and inter-group correction with the calculators (the multiplier 601, the subtractor 602, the differentiator 607, the multiplier 606, and the subtractor 605) by using respective new correction coefficient values which are obtained through the addition process. In this case, the new gain correction coefficient value may be a value obtained by multiplying an intra-group gain correction coefficient value by an inter-group gain correction coefficient value. Further, the new DC offset correction coefficient value may be a value obtained by adding an intra-group DC offset correction coefficient value by an inter-group DC offset correction coefficient value. Similarly, the new sampling timing correction coefficient value may be a value obtained by adding an intra-group sampling timing correction coefficient value by an inter-group sampling timing correction coefficient value.

What is claimed is:

1. A medical diagnostic signal detection apparatus comprising:
   a first amplifier;
   a first analog-digital converter whose input side is electrically connected to an output side of the first amplifier;
   second and third amplifiers;
   second and third analog-digital converters whose input sides are respectively electrically connected to output sides of the second and third amplifiers, the first to third amplifiers and the first to third analog-digital converters forming a first group and being integrated on a first semiconductor substrate;
   a fourth amplifier;
   a fourth analog-digital converter whose input side is electrically connected to an output side of the fourth amplifier;
   fifth and sixth amplifiers;
   fifth and sixth analog-digital converters whose input sides are respectively electrically connected to output sides of the fifth and sixth amplifiers, the fourth to sixth amplifiers and the fourth to sixth analog-digital converters forming a second group and being integrated on a second semiconductor substrate or the first semiconductor substrate;

an inter-group correction signal generator whose output is input to the first and fourth amplifiers;

first to fourth medical diagnostic signal detectors that respectively detect first to fourth medical diagnostic signals, outputs of the first to fourth medical diagnostic signal detectors being respectively input to the second, third, fifth and sixth amplifiers;

first inter-group correction coefficient search means connected to an output side of the fourth analog-digital converter forming a master channel of the second group; and first and second inter-group correction means respectively connected to output sides of the fifth and sixth analog-digital converters, wherein an output of the fourth analog-digital converter and an output of the first analog-digital converter forming a top master channel are input to the first inter-group correction coefficient search means, wherein the first inter-group correction coefficient search means searches for a first mismatch amount regarding a gain, a DC offset, a sampling timing, or a frequency bandwidth of a circuit in the second group relative to a circuit in the first group through comparison between two input values, so as to obtain a first correction coefficient which is used to correct the gain, the DC offset, the sampling timing, or the frequency bandwidth of the circuit in the second group and is proportional or directly proportional to the first mismatch amount, wherein the first correction coefficient is input to the first and second inter-group correction means, and wherein the first and second inter-group correction means perform inter-group correction on outputs of the fifth and sixth analog-digital converters through digital addition calculation, digital subtraction calculation, digital multiplication calculation, or digital division calculation using the first correction coefficient.

2. The medical diagnostic signal detection apparatus according to claim 1, further comprising:

first and second intra-group correction means respectively connected to the output sides of the fifth and sixth analog-digital converters;

an intra-group correction signal generator; and first and second intra-group correction coefficient search means, wherein, during an intra-group correction coefficient search, an output of the intra-group correction signal generator is input to the fourth, fifth and sixth amplifiers, wherein, during the intra-group correction coefficient search, an output of the fifth analog-digital converter and an output of the fourth analog-digital converter forming the master channel of the second group are input to the first intra-group correction coefficient search means, wherein the first intra-group correction coefficient search means searches for a second mismatch amount regarding a gain, a DC offset, or a frequency bandwidth of the fifth amplifier relative to the fourth amplifier, or a third mismatch amount regarding a gain, a DC offset, a sampling timing, or a frequency bandwidth of the fifth analog-digital converter relative to the fourth analog-digital converter, through comparison between the two input values, so as to obtain a first intra-group correction coefficient which is proportional or directly proportional to the second or third mismatch amount, wherein, in a period in which the third medical diagnostic signal is received, the first intra-group correction means performs intra-group correction on the output of the fifth analog-digital converter through digital addition calculation, digital subtraction calculation, digital multiplication calculation, or digital division calculation using the first intra-group correction coefficient, wherein, during the intra-group correction coefficient search, an output of the sixth analog-digital converter and the output of the fourth analog-digital converter forming the master channel of the second group are input to the second intra-group correction coefficient search means, wherein the second intra-group correction coefficient search means searches for a fourth mismatch amount regarding a gain, a DC offset, or a frequency bandwidth of the sixth amplifier relative to the fourth amplifier, or a fifth mismatch amount regarding a gain, a DC offset, a sampling timing, or a frequency bandwidth of the sixth analog-digital converter relative to the fourth analog-digital converter, through comparison between the two input values, so as to obtain a second intra-group correction coefficient which is proportional or directly proportional to the fourth or fifth mismatch amount, and wherein, in a period in which the fourth medical diagnostic signal is received, the second intra-group correction means performs intra-group correction on the output of the sixth analog-digital converter through digital addition calculation, digital subtraction calculation, digital multiplication calculation, or digital division calculation using the second intra-group correction coefficient.

3. The medical diagnostic signal detection apparatus according to claim 1, wherein the first inter-group correction coefficient search means searches for the first mismatch amount so as to obtain the first correction coefficient in a background in which at least one of the first to fourth medical diagnostic signal detectors, at least one of the second, third, fifth and sixth amplifiers, and at least one of the second, third, fifth and sixth analog-digital converters receive at least one of the first to fourth medical diagnostic signals.

4. The medical diagnostic signal detection apparatus according to claim 2, wherein the first inter-group correction coefficient search means searches for the first mismatch amount so as to obtain the first correction coefficient in a background in which at least one of the first to fourth medical diagnostic signal detectors, at least one of the second, third, fifth and sixth amplifiers, and at least one of the second, third, fifth and sixth analog-digital converters receive at least one of the first to fourth medical diagnostic signals.

5. The medical diagnostic signal detection apparatus according to claim 4, wherein the intra-group correction coefficient search is made in a period in which neither of the first and second medical diagnostic signals are received, or neither of the third and fourth medical diagnostic signals are received.

6. The medical diagnostic signal detection apparatus according to claim 1, wherein the medical diagnostic signal detection apparatus is an ultrasonic diagnostic main body apparatus, an ultrasonic diagnostic probe, or an X-ray CT apparatus.

7. The medical diagnostic signal detection apparatus according to claim 2, wherein the medical diagnostic signal detection apparatus is an ultrasonic diagnostic main body apparatus, an ultrasonic diagnostic probe, or an X-ray CT apparatus.

8. The medical diagnostic signal detection apparatus according to claim 1, further comprising:

a transmission circuit that transmits a signal which is a source of the medical diagnostic signal, wherein the first mismatch regarding the gain, the DC offset, the sampling timing, or the frequency bandwidth is caused by a temperature fluctuation due to heat generation resulting from a power loss of the transmission circuit.

9. The medical diagnostic signal detection apparatus according to claim 2, further comprising:
a transmission circuit that transmits a signal which is a source of the medical diagnostic signal,
wherein the first mismatch regarding the gain, the DC offset, the sampling timing, or the frequency bandwidth is caused by a temperature fluctuation due to heat generation resulting from a power loss of the transmission circuit.

10. A medical diagnostic signal detection method for a medical diagnostic signal detection apparatus including a first amplifier; a first analog-digital converter whose input side is electrically connected to an output side of the first amplifier; second and third amplifiers; second and third analog-digital converters whose input sides are respectively electrically connected to output sides of the second and third amplifiers, the first to third amplifiers and the first to third analog-digital converters forming a first group and being integrated on a first semiconductor substrate; a fourth amplifier; a fourth analog-digital converter whose input side is electrically connected to an output side of the fourth amplifier; fifth and sixth amplifiers; fifth and sixth analog-digital converters whose input sides are respectively electrically connected to output sides of the fifth and sixth amplifiers, the fourth to sixth amplifiers and the fourth to sixth analog-digital converters forming a second group and being integrated on a second semiconductor substrate or the first semiconductor substrate; an inter-group correction signal generator whose output is input to the first and fourth amplifiers; first to fourth medical diagnostic signal detectors that respectively detect first to fourth medical diagnostic signals, outputs of the first to fourth medical diagnostic signal detectors being respectively input to the second, third, fifth and sixth amplifiers; first inter-group correction coefficient search means connected to an output side of the fourth analog-digital converter forming a master channel of the second group; and first and second inter-group correction means respectively connected to output sides of the fifth and sixth analog-digital converters, the method comprising:
inputting an output of the fourth analog-digital converter and an output of the first analog-digital converter forming a top master channel to the first inter-group correction coefficient search means;
causing the first inter-group correction coefficient search means to search for a first mismatch amount regarding a gain, a DC offset, a sampling timing, or a frequency bandwidth of a circuit in the second group relative to a circuit in the first group through comparison between two input values, so as to obtain a first correction coefficient which is used to correct the gain, the DC offset, the sampling timing, or the frequency bandwidth of the circuit in the second group and is proportional or directly proportional to the first mismatch amount;
inputting the first correction coefficient to the first and second inter-group correction means; and
causing the first and second inter-group correction means to perform inter-group correction on outputs of the fifth and sixth analog-digital converters through digital addition calculation, digital subtraction calculation, digital multiplication calculation, or digital division calculation using the first correction coefficient.

11. The medical diagnostic signal detection method according to claim 10,
wherein the medical diagnostic signal detection apparatus further includes
first and second intra-group correction means respectively connected to the output sides of the fifth and sixth analog-digital converters;
an intra-group correction signal generator; and
first and second intra-group correction coefficient search means,
wherein, during an intra-group correction coefficient search, an output of the intra-group correction signal generator is input to the fourth, fifth and sixth amplifiers,
wherein, during the intra-group correction coefficient search, an output of the fifth analog-digital converter and an output of the fourth analog-digital converter forming the master channel of the second group are input to the first intra-group correction coefficient search means,
wherein the first intra-group correction coefficient search means searches for a second mismatch amount regarding a gain, a DC offset, or a frequency bandwidth of the fifth amplifier relative to the fourth amplifier, or a third mismatch amount regarding a gain, a DC offset, a sampling timing, or a frequency bandwidth of the fifth analog-digital converter relative to the fourth analog-digital converter, through comparison between the two input values, so as to obtain a first intra-group correction coefficient which is proportional or directly proportional to the second or third mismatch amount,
wherein, in a period in which the third medical diagnostic signal is received, the first intra-group correction means performs intra-group correction on the output of the fifth analog-digital converter through digital addition calculation, digital subtraction calculation, digital multiplication calculation, or digital division calculation using the first intra-group correction coefficient,
wherein, during the intra-group correction coefficient search, an output of the sixth analog-digital converter and the output of the fourth analog-digital converter forming the master channel of the second group are input to the second intra-group correction coefficient search means,
wherein the second intra-group correction coefficient search means searches for a fourth mismatch amount regarding a gain, a DC offset, or a frequency bandwidth of the sixth amplifier relative to the fourth amplifier, or a fifth mismatch amount regarding a gain, a DC offset, a sampling timing, or a frequency bandwidth of the sixth analog-digital converter relative to the fourth analog-digital converter, through comparison between the two input values, so as to obtain a second intra-group correction coefficient which is proportional or directly proportional to the fourth or fifth mismatch amount, and
wherein, in a period in which the fourth medical diagnostic signal is received, the second intra-group correction means performs intra-group correction on the output of the sixth analog-digital converter through digital addition calculation, digital subtraction calculation, digital multiplication calculation, or digital division calculation using the second intra-group correction coefficient.

12. The medical diagnostic signal detection method according to claim 10,
wherein the first inter-group correction coefficient search means searches for the first mismatch amount so as to obtain the first correction coefficient in a background in which at least one of the first to fourth medical diagnostic signal detectors, at least one of the second, third, fifth and sixth amplifiers, and at least one of the second, third, fifth and sixth analog-digital converters receive at least one of the first to fourth medical diagnostic signals.

13. The medical diagnostic signal detection method according to claim 11,
wherein the first inter-group correction coefficient search means searches for the first mismatch amount so as to obtain the first correction coefficient in a background in which at least one of the first to fourth medical diagnostic signal detectors, at least one of the second, third, fifth and sixth amplifiers, and at least one of the second, third, fifth and sixth analog-digital converters receive at least one of the first to fourth medical diagnostic signals.

14. The medical diagnostic signal detection method according to claim 13,
wherein the intra-group correction coefficient search is made in a period in which neither of the first and second medical diagnostic signals are received, or neither of the third and fourth medical diagnostic signals are received.

15. The medical diagnostic signal detection apparatus according to claim 1, further comprising:
an intra-group correction signal generator; and
first and second intra-group correction coefficient search means,
wherein, during an intra-group correction coefficient search, an output of the intra-group correction signal generator is input to the fourth, fifth and sixth amplifiers,
wherein, during the intra-group correction coefficient search, an output of the fifth analog-digital converter and an output of the fourth analog-digital converter forming the master channel of the second group are input to the first intra-group correction coefficient search means,
wherein the first intra-group correction coefficient search means searches for a second mismatch amount regarding a gain, a DC offset, or a frequency bandwidth of the fifth amplifier relative to the fourth amplifier, or a third mismatch amount regarding a gain, a DC offset, a sampling timing, or a frequency bandwidth of the fifth analog-digital converter relative to the fourth analog-digital converter, through comparison between the two input values, so as to obtain a first intra-group correction coefficient which is proportional or directly proportional to the second or third mismatch amount,
wherein, in a period in which the third medical diagnostic signal is received, the first inter-group correction means performs inter-group correction and intra-group correction on the output of the fifth analog-digital converter through digital addition calculation, digital subtraction calculation, digital multiplication calculation, or digital division calculation using the first correction coefficient and the first intra-group correction coefficient,
wherein, during the intra-group correction coefficient search, an output of the sixth analog-digital converter and the output of the fourth analog-digital converter forming the master channel of the second group are input to the second intra-group correction coefficient search means,
wherein the second intra-group correction coefficient search means searches for a fourth mismatch amount regarding a gain, a DC offset, or a frequency bandwidth of the sixth amplifier relative to the fourth amplifier, or a fifth mismatch amount regarding a gain, a DC offset, a sampling timing, or a frequency bandwidth of the sixth analog-digital converter relative to the fourth analog-digital converter, through comparison between the two input values, so as to obtain a second intra-group correction coefficient which is proportional or directly proportional to the fourth or fifth mismatch amount, and
wherein, in a period in which the fourth medical diagnostic signal is received, the second inter-group correction means performs inter-group correction and intra-group correction on the output of the sixth analog-digital converter through digital addition calculation, digital subtraction calculation, digital multiplication calculation, or digital division calculation using the first correction coefficient and the second intra-group correction coefficient.

* * * * *